(12) United States Patent
Hung

(10) Patent No.: US 6,610,484 B1
(45) Date of Patent: *Aug. 26, 2003

(54) IDENTIFYING MATERIAL FROM A BREAST DUCT

(75) Inventor: David T. Hung, Belmont, CA (US)

(73) Assignee: Cytyc Health Corporation, Boxborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/625,399

(22) Filed: Jul. 26, 2000

Related U.S. Application Data

(63) Continuation-in-part of application No. 09/502,404, filed on Feb. 10, 2000, which is a continuation-in-part of application No. 09/313,463, filed on May 17, 1999, application No. 09/625,399, which is a continuation-in-part of application No. 09/473,510, filed on Dec. 28, 1999, now Pat. No. 6,413,228.

(60) Provisional application No. 60/166,100, filed on Nov. 17, 1999, and provisional application No. 60/117,281, filed on Jan. 26, 1999.

(51) Int. Cl.$^7$ .................................................. C12Q 3/00
(52) U.S. Cl. ........................... 435/6; 435/7.1; 435/7.2; 435/7.23; 435/7.92; 436/63; 436/64; 436/501; 436/503; 436/504
(58) Field of Search ........................... 435/7.1, 7.2, 7.4, 435/7.23, 7.92, 7.93, 7.94, 7.95, 6; 436/63, 64, 501, 503, 504

(56) References Cited

U.S. PATENT DOCUMENTS

| | | | |
|---|---|---|---|
| 4,782,015 A | 11/1988 | Allison et al. | |
| 5,478,556 A | 12/1995 | Elliott et al. | |
| 5,652,115 A | 7/1997 | Marks et al. | |
| 5,763,415 A | 6/1998 | Sukumar | |
| 5,798,266 A | 8/1998 | Quay et al. | |
| 5,914,238 A | 6/1999 | Keesee et al. | |

FOREIGN PATENT DOCUMENTS

| | | |
|---|---|---|
| EP | 0319686 | 6/1989 |
| WO | WO 97/05898 | 2/1997 |
| WO | WO 00/70349 | 11/2000 |

OTHER PUBLICATIONS

Hou et al Radiology vol. 195 p. 568 (1995).*
Azavedo et al., Anticancer Research 6:263–266, 1986.*
Database Embase on Dialog. No. 06717313, Chinese Journal of Clinical Oncology 23/6:381–385, 1996.*
Barnes and Masood, "Potential value of hormone receptor assay in carcinoma in situ of breast"A.J.C.P., Nov. 1990, vol. 94, No. 5, 5, 533–537.
Barnes et al. "Low nm23 protein expression in infiltrating ductal breast carcinomas correlates with reduced patient survival" Am J. Path; vol. 139, No. 2, 8/91.
Berntsen et al. "Influence of Treatment with Aminoglutethimide on Plasma and Red–Blood–Cell Glutathione Status in Breast Cancer Patients." Cancer Chemother Pharmacol. 1998. vol. 42, pp. 46–51.
Boccuzzi et al. "Breast Duct Fluid Dehydroepiandrosterone sulphate in Fibrocystic Disease." European J. Cancer And Clinical Oncology. Aug. 1987. vol. 23, pp. 1099–1102.
"Cancer detection techniques shown." Santa Barbara News Press Aug. 3, 1971.
Cassels, "New test may speed breast cancer detection." The Medical Post Mar. 20, 1973.
Ernster et al. "Benign and malignant breast disease: initial study results of serum and breast fluid analyses of endogenous estrogens." JNCI vol. 79 No. 5.
Fabian, et al. "Biomarker and cytologic abnormalities in women at high and low risk for breast cancer" J of Cellular Biochemistry 17G:153–160 (1993).
Fabian, et al. "Prevalence of abnormal biomarkers in fine needle breast aspirates in high risk populations." 1993 Proc. Ann Meeting Am Assoc. Cancer Res. 34:A1556.
"Finding asymptomatic breast cancer." Medical World News Jul. 23, 1971.
Fryckberg, et al. "Ductal carcinoma in situ of the breast." Surgery, Gynecology & Obstetrics Oct. 1993 vol. 177.
Gilbert, et al. "A pilot study of Pi–class glutathione s–transferase expression in breast cancer: correlation with estrogen receptor expression and prognosis in node–negative breast cancer." J. of Clin Oncology, vol. 11, No. 1 1/93:pp. 49–58.
Goodson & King. "Discharges and secretions of the nipple. The Breast, Comprehensive management of benign and malignant diseases"2nd ed vol. 2. 1998.
Head et al. assessment of immulogic competence and host reactivity against tumor antigens in breast cancer with vaccines. vol. 690 of theAnnals of the NY Academy of Sciences Aug. 12, 1993.
Imayama, et al. "Presence of elevated carcinoembryonic antigen on absorbent disks applied to nipple are of breast carcinoma patients." Cancer Sep. 15, 1996 vol. 78 No. 6.
JAMA May 7, 1973; vol. 224, No. 6 pp. 823–827.
King, et al. "Analytic studies of foam cells from breast cancer precursors." Cytometry 5:124–130 (1984).
King, et al. "Cellular composition of the nipple aspirate specimen of fluid." AJCP vol. 64 Dec. 1975 pp. 728–738.
Kristensen et al. "A rare CYP19 (aromatase) variant may increase the risk of breast cancer." Pharmacogenetics. 1998. vol. 8, pp. 43–48.

(List continued on next page.)

*Primary Examiner*—Sheela Huff
(74) *Attorney, Agent, or Firm*—Banner & Witcoff, Ltd.

(57) ABSTRACT

Methods and systems for identifying material from a breast duct using one or more markers that can be identified in ductal fluid retrieved from the breast are provided.

23 Claims, No Drawings

OTHER PUBLICATIONS

Lobsenz. "A new way to detect breast cancer early." Good House Keeping Jan. 1975.

Love et al., "Breast–duct Endoscopy to Study Stages of Cancerous Breast Disease." Oct. 12, 1996. vol. 348 pp. 997–999.

Love. "Collection and analysis of nipple aspirate fluid in the early detection of breast cancer." Windy Hill Technology, Inc. NAF Focus Group Study Sep. 18, 1998.

Lu et al. "The Effects of Aromatase Inhibitors and Antiestrogens in the Nude Mouse Model." Breast Cancer Research and Treatment 1998. vol. 50, pp. 63–71.

Masood & Johnson. "The value of imprint cytology in cytochemocal detection steroid hormone receptors in breast cancer." AJCP vol. 87 No. 1 pp. 30–36.

Masood, et al. "Breast health Challenges and Promises." J. Florida M.A. Aug./Sep. 1996/vol. 83, No. 7 pp. 459–465.

Masood, "Fluorescent cytochemical detection of estrogen and progesterone receptors in breast fine–needle aspirates." AJCP Jan. 1991.

Masood. "The missing link: a 'pap smear' for early breast cancer detection and prevention." The Breast Journal, vol. 5 No. 1, 1999 pp. 1–2.

Nass, et al. "Breast cancer biology blossoms in the clinic." Nature Medicine vol. 4 No. 7 Jul. 1998.

Newman, et al, J Natl Cancer Inst. Dec. 1979 63(6):1339–46.

North, et al. "Vasopressin gene related products are markers of human breast cancer." Breast Cancer Research and Treatment 34:229–235, 1995.

Okazaki, et al "Relationship between cytologic results and the extent of intraductal spread in nonpalpable breast cancers with nipple dischage" Tumor Res. 31, 89–97 (1996).

Papanicolaou et al. "Exfoliative cytology of the human mammary gland and its value in the diagnosis of cancer and other diseases of the breast." Cancer Mar.–Apr. 1958, 11(2):377–409.

Pertschuk et al. "Estrogen receptor immunochemistry in endometrial carcinoma." Gynecologic Oncology 63, 28–33 (1996) pp. 28–33.

Petrakis & King. "Genetic markers and cancer epidemiology." Cancer Apr. supp 1977 vol. 39 pp. 1861–1866.

Petrakis et al. "Epithelial dysplasia in nipple aspirates of breast fluid: association with family history and other breast cancer risk factors." JNCI vol. 68 No. 1 Jan. 1982.

Petrakis; "Nipple apsirate fluid in epidemiologic studies of breast disease." Epidemiologic Reviews vol. 15 No. 1 1993.

Phillips, et al. "Nipple Aspirate Fluid in Relation to breast Cancer." The Breast. Aug. 1999, vol. 8, No. 4, pp. 169–174.

Rose, et al. "A Comparison of Serum and Breast Duct Fluid Immunoassayable prolactin and Growth Hormon Woman and and Patients with Cystic Breast Disease." Cancer, Dec. 1, 1987. vol. 60, No. 11, pp. 2761–2765.

Rose. "Hormones and Growth factors in Nipple aspirates from normal women and benign breast disease patients." Cancer Detection and Prevention vol 16, Issue 1 1992.

Rosner et al. "Diagnosis of breast carcinoma with radiolabeled monoclonal antibodies to carcinomebryonic antigen and human milk fat globulin." Cancer Investigation, 13(6), 573–582 (1995).

Sartorius et al. "The biochemistry of breast cysts fluids and duct secretions." Breast Cancer Research and Treatment 35:255–266 1995.

Sartorius, "Cytologic evaluation of breast fluid in the detection of breast disease" J Nat'l Cancer Inst vol. 59 No. 4 Oct. 1977 pp. 1073–1080.

Sauter et al, "Nipple aspirate fluid: a promising non–invasive method to identify cellular markers of breast cancer risk" 1997 British J. Cancer 76(4):494–501.

Sauter et al. Prostate specific antigen levels in nipple aspirate fluid correlate with breast cancer risk, Cancer Epidemiology vol. 5, 967–970, Dec. 1996.

Strah & Love. "The in situ carcinomas of the breast." JAMWA vol. 47 No. 5 Sep./Oct. 1992.

Sukumar & McKenzie, "Molecular genetics of human breast cancer." Cellular and molecular mechanisms of hormonal carcinogenesis: Environmental influences, ISBN 0–471–02202–0 1996.

Sukumar & McKenzie, "Breast cancer prevention strategies for the twenty first century" Molecular Medicine Today Nov. 1996.

Vetvicka, et al. "Human breast milk contains procathepsin D–detection by specific antibodies." Biochemistry and Molecular Biology International vol. 30, No. 5, Aug. 1993 pp. 921–928.

Vorherr, H. "Endocrinology of Breast Cancer." Maturitas. 1987. vol. 9, pp. 113–122.

Wrensch, et al. "Breast cancer risk associated with abnormal cytology in nipple aspirates of breast fluid and prior history of breast biopsy." Am J. of Epidemiology vol. 137 No. 8 1993.

Wrensch, et al. "Breast cancer incidence in women with abnormal cytology in nipple aspirates of breast fluid" Am. J. of Epidemiology vol. 135 No. 2 1992.

Wynder et al. "Breast Secretion in Finnish Women: a metabolic epidemiologic study," Cancer 47: 1444–1450, 1981.

Wynder et al, "Prolactin Oestrogen, and Lipids in Breast Fluid." The Lancet Oct. 22, 1977. vol. 2 No. 8043, pp. 840–842.

Zippin & Petrakis, "Identification of high risk groups in breast cancer." Cancer vol. 28 pp. 1381–1387 Dec. 1971.

Hou et al Radiology vol. 195 p. 568 (1995).*

* cited by examiner

US 6,610,484 B1

IDENTIFYING MATERIAL FROM A BREAST DUCT

CROSS-REFERENCES TO RELATED APPLICATIONS

This application is a continuation-in-part of application Ser. No. 09/502,404, filed on Feb. 10, 2000, which was a continuation-in-part of application Ser. No. 09/313,463, filed on May 17, 1999, which claimed the benefit of provisional application No. 60/117,281, filed on Jan. 26, 1999. This application is also a continuation-in-part of application Ser. No. 09/473,510, filed on Dec. 28, 1999 now U.S. Pat. No. 6,413,228. This application also claims the benefit under 37 CFR 1.78 of provisional application No. 60/166,100 filed on Nov. 17, 1999. The full disclosures of each of the prior applications are incorporated herein by reference.

BACKGROUND OF THE INVENTION

1. Field of the Invention

The field of this invention is methods and systems for detecting breast cancer and breast precancer in humans.

2. Description of the Background Art

For several decades significant members of the medical community dedicated to studying breast cancer have believed and shown that the cytological analysis of cells retrieved from nipple discharge from the breast milk ducts can provide valuable information leading to an identifying patients at risk for breast cancer. Indeed Papanicolaou himself contributed to the genesis of such a possibility of a "Pap" smear for breast cancer by analyzing the cells contained in nipple discharge. See Papanicolaou et al, "Exfoliative Cytology of the Human Mammary Gland and Its Value in the Diagnosis of Cancer and Other Diseases of the Breast" Cancer (1958) March/April 377–409. See also Petrakis, "Physiological, biochemical, and cytological aspects of nipple aspirate fluid", *Breast Cancer Research and Treatment* 1986; 8:7–19; Petrakis, "Studies on the epidemiology and natural history of benign breast disease and breast cancer using nipple aspirate fluid" *Cancer Epidemiology, Biomarkers and Prevention* (January/Febuary 1993) 2:3–10; Petrakis, "Nipple Aspirate Fluid in epidemiological studies of breast disease", *Epidemiologic Reviews* (1993) 15:188–195. More recently, markers have also been detected in nipple fluid. See Sauter et al, "Nipple aspirate fluid: a promising non-invasive method to identify cellular markers of breast cancer risk", *British Journal of Cancer* 76(4):494–501 (1997). The detection of CEA in fluids obtained by a nipple blot is described in Imayama et al. (1996) *Cancer* 78: 1229–1234.

Breast cancer is believed to originate in the lining of a single breast milk duct in the breast; and additionally human breasts are believed to contain from 6 to 9 of these ducts. See Sartorius, *JAMA* 224 (6): 823–827 (1973). Sartorius describes use of hair-like single lumen catheters that are inserted into breast ducts using an operating microscope and the ducts were flushed with saline solution as described in Cassels, D Mar. 20, 1973, *The Medical Post*, article entitled "New tests may speed breast cancer detection". Sartorius et al, Contrast ductography for recognition and localization of benign and malignant breast lesions: an improved technique. pp. 281–300. In: Logan WW, ed. *Breast Carcinoma* New York, Wiley, 1977. After the fluid was infused, the catheter was removed because it was too small to collect the fluid, the breast was squeezed and fluid that oozed onto the nipple surface was removed from the surface by a capillary tube. Similarly, Love and Barsky, "Breast-duct endoscopy to study stages of cancerous breast disease", *Lancet* 348(9033):997–999, 1996 describes cannulating breast ducts with a single lumen catheter and infusing a small amount of saline, removing the catheter and squeezing to collect the fluid that returns on the nipple surface. The use of a rigid 1.2 mm ductscope to identify intraductal papillomas in women with nipple discharge is described in Makita et al (1991) *Breast Cancer Res Treat* 18: 179–188. It would be advantageous to develop methods and devices to collect the ductal fluid from within the duct.

Galactography, or contrast ductography has for years located breast ducts based on spontaneous nipple discharge, infused the ducts (using cannulas for this purpose) with contrast dye solutions, and taken x-ray pictures to determine the source of the discharge within the duct. See generally, The Breast: Comprehensive Management of Benign and Malignant Breast Diseases, Bland and Copeland eds. W.B. Saunders Co. Philadelphia Pa. 1991 pages 61–67.

Nuclear matrix proteins are implicated in bladder, colon, prostate, breast and other cancers, and have been put forth by Matritech, Inc (Newton, Mass. 02460) as part of a kit for testing for bladder cancer using body fluid. For testing for breast cancer, a blood test has been developed using antibodies to nuclear matrix proteins (see website for Matritech, Inc. http://www.matritech.com) The blood and body fluid tests are promoted as being capable of early detection of the cancers they seek to identify. In addition, profiles and differential patterns of expression of nuclear matrix proteins have been detected for several different cancers (Fey and Penman 1986, Stuurman 1990, and Getzenberg 1990).

Matritech, Inc. has patented various aspects of proteins and nucleic acids of nuclear matrix proteins as well as kits for testing for their presence in order to identify cancer in U.S. Pat. Nos. 5,965,376, 5,914,238, 5,882,876, 5,858,683, 5,840,503, 5,830,677, 5,783,403, 5,780,596, 5,698,439, 5,686,562, and 5,547,928. Specifically, Matritech has patented claims in U.S. Pat. No. 5,914,238 to a method for diagnosing breast cancer in a patient comprising detecting the presence of a breast cancer-associated protein in a tissue or body fluid obtained from the patient. The breast cancer-associated protein has a molecular weight of about 32,500 or 33,000 Daltons and an isoelectric point of about 6.82, and has a continuous amino acid sequence from several amino acid sequences disclosed in the application. The nuclear matrix protein is detected by polyclonal or monoclonal antibodies or by PCR amplification of an expression product of the target gene. The patient sample in the examples is breast tissue samples, although the possibility of testing blood or body fluid is claimed and mentioned in the specification. Testing breast duct fluid is not described.

SUMMARY OF THE INVENTION

An object of the invention is to identify a patient having breast cancer or breast precancer. In accordance with this object, is provided a method comprising providing a ductal fluid sample from one duct of a breast of a patient, the fluid not mixed with ductal fluid from any other duct of the breast, and examining the ductal fluid sample to determine the presence of a marker comprising a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules. In accordance with this object is also provided methods for determining markers which can identify a patient having breast cancer or precancer by examining the ductal fluid sample to determine the presence of a marker comprising RNA, DNA, protein, polypeptide, or peptide form of the marker. The invention also includes a method of identifying a patient having breast cancer or breast precancer, said method comprising providing a ductal fluid sample from one duct of a breast of a patient, said fluid not mixed with ductal fluid from any other duct of the breast, examining the ductal fluid sample to determine the presence of a marker comprising a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules; wherein the marker is capable of differentiating between any two of cytological categories consisting of normal, abnormal, hyperplasia, atypia, ductal carcinoma, ductal carcinoma in situ (DCIS), ductal carcinoma in situ—low grade (DCIS-LG), ductal carcinoma in situ—high grade (DCIS-HG), invasive carcinoma, atypical mild changes, atypical marked changes, atypical ductal hyperplasia (ADH), insufficient cellular material for diagnosis, and sufficient cellular material for diagnosis.

Any of the methods can comprise further analyzing the ductal fluid for abnormal cytology. Any of the methods can comprise that the ductal fluid is retrieved by placing a ductal access tool in the duct and infusing fluid into the duct through the tool and retrieving from the accessed duct through the tool a portion of the infused fluid mixed with ductal fluid. The method can be repeated for more than one duct on a breast; for example, the method can be practiced comprising a plurality of ducts on a breast.

The invention provides additionally, a method for identifying a patient having breast cancer or breast precancer, by providing a ductal fluid sample from at least one duct of a breast of the patient; and examining the ductal fluid sample to determine the presence of a marker comprising an expression product of a gene encoding a nuclear matrix protein. The expression product can comprise a nucleic acid or a polypeptide. The expression product can comprise RNA, or a protein or a part of a protein. The nuclear matrix protein can be lamin A, lamin B, lamin C, a peripheral matrix protein, nuclear mitotic spindle apparatus protein (NuMA), topoisomerase II, or an internal nuclear matrix protein. The expression product can be a polypeptide and examining can comprise contacting the polypeptide marker with an antibody that specifically binds a portion of the polypeptide. The expression product can be a nucleic acid and examining can comprise detecting the presence of the nucleic acid. Detecting the presence of the nucleic acid can comprise amplifying the nucleic acid. Providing the ductal fluid sample can comprise obtaining the sample from the breast. Providing the ductal fluid sample can comprise receiving a sample that had been previously obtained. The fluid can be obtained by nipple aspiration of the milk ducts. The fluid sample can be obtained by washing the ductal lumen and retrieving fluid and cells from the lumen. The fluid collected can be from a single duct. The fluid can be collected from a plurality of ducts.

The invention also provides systems for diagnosing breast cancer or precancer comprising a tool to retrieve ductal fluid from a breast duct and instructions for use to determine the presence of a marker.

DETAILED DESCRIPTION OF PREFERRED EMBODIMENTS OF THE INVENTION

The following preferred embodiments and examples are offered by way of illustration and not by way of limitation.

The method of the invention provides a method of screening women for breast cancer or precancer comprising providing a ductal fluid sample from at least one duct of a breast of the patient; and detecting an increased level of a marker wherein an increased level of one or more markers indicates an increased risk for breast cancer or precancer.

The method is practiced by providing a ductal fluid sample from at least one duct of a breast of the patient. Providing the ductal fluid sample can comprise obtaining the sample from the breast. Providing the ductal fluid sample can also comprise receiving a sample that had been previously obtained. For example, a laboratory can receive a ductal fluid sample from a patient or a practitioner, and the laboratory can be directed to make an analysis of the sample. Where the fluid is obtained from the breast, the fluid sample can be obtained e.g. by nipple aspiration of the milk ducts or by ductal lavage of at least one breast milk duct. When fluid is collected by nipple aspiration, or by ductal lavage, the fluid can be collected from a single duct. For example the duct and the collection tube can be marked so that the analysis of the fluid is traceable to one duct.

By the procedure of ductal lavage, ductal epithelial cells that line the walls of the ductal lumen are washed out of the duct. Lavage or wash fluid is infused into the duct, and the lavage fluid mixed with ductal fluid is collected. Lavage is described in copending and co-owned applications including Ser. Nos. 09/067,661, 09/301,058, PCT US99/09141, No. 60/122,076, Ser. No. 09/313,463, No. 60/143,359, and U.S. application Ser. No. 09/473,510, all incorporated by reference in their entirety. In some cases suction can be applied to the tool accessing the ductal lumen in order to retrieve a maximum amount of cells and/or fluid. Lavage or wash fluid can be infused into the duct, and collected. Suction can be applied to the tool accessing the ductal lumen in order to retrieve a maximum amount of cells and/or fluid.

Access of a breast duct can be facilitated as described in e.g. Love & Barsky, (1996) *Lancet* 348: 997–999, Makita et al (1991) *Breast Cancer Res Treat* 18: 179–188, or Okazaki et al (1991) *Jpn J. Clin. Oncol.* 21:188–193. Alternatively, ductal fluid can be retrieved by a medical tool, e.g. a catheter or a cannula placed into the duct to infuse wash fluid to retrieve a mixture of wash and ductal fluids. The fluid from the breast duct can contain ductal epithelial cells, including cells of a stage considered to be precancerous or cancerous.

Nipple aspiration of breast ductal fluid is achieved by using vacuum pressure. Nipple aspiration techniques are also described and claimed in co-pending and co-owned patent application U.S. patent application Ser. No. 09/438, 219, herein incorporated by reference in their entirety. Nipple aspirate fluid can be retrieved as described in e.g. Goodson W H & King E B, *Chapter 4: Discharges and Secretions of the Nipple,* The Breast: Comprehensive Management of Benign and Malignant Diseases (1998) $2^{nd}$ Ed. vol 2, Bland & Kirby eds. W.B. Saunders Co, Philadelphia, Pa. pp. 51–74; Wrensch et al., (1992) American Journal of Epidemiology. 135(2):130–41; and Sauter et al (1997) British Journal of Cancer. 76(4):494–501. Ductal lavage is described in copending patent application U.S. Ser. No. 09/067,661 filed Apr. 28, 1998. Cells of the lesion can be retrieved by collecting the ductal fluid that contains some of these cells, e.g. by aspirating the nipple to obtain nipple aspirate fluid, e.g. as described in Petrakis (1993) *Cancer Epidem. Biomarker Prev.* 2:3–10, Petrakis (1986) *Breast Cancer Res. Treat* 8: 7–19, Wrensch et al (1992) *Am. J. Epidem.* 135:130–141, Wrensch et al (1990) *Breast Cancer Res Treat* 15: 39–21, and Wrensch et al (1989) *Cancer Res.* 49: 2168–2174. Also fluid secretions from the nipple can be collected as they spontaneously appear on the nipple surface. In order to collect the fluid not mixed with ductal fluid from other ducts, a practitioner carefully watches for the signs of fluid and retrieves the fluid from the nipple surface near the orifice before it has a chance to mix with fluid from any other orifice.

The ductal fluid may be analyzed in situ, i.e. inside the breast and inside the breast duct, e.g. where a particular marker can be introduced into the duct and can be identified from within the breast. In situ testing within the duct is also considered a non-invasive means of examining the ductal epithelial cells. Ductal epithelial cells that are examined by the method of the invention can be examined in situ (i.e. in the duct; e.g. where a marker can bind the cells or a component of the cells in the duct and be identified from within the breast by a tag attached to the marker), or after the ductal epithelial cells have been removed from the breast of the patient by non-invasive means, e.g. as just described. Methods of in situ analysis can include use of such molecular biology tools, methods, and materials as described in e.g. U.S. Pat. Nos. 5,169,774, 5,720,937, 5,677,171, 5,720,954, 5,725,856, 5,770,195, and 5,772,997. Markers to breast cancer and breast precancer described elsewhere and herein may also be used for an in situ analysis of the breast duct.

The ductal fluid is examined to detect the presence of precancerous or cancerous ductal epithelial cells. The fluid sample (comprising ductal epithelial cells) can be analyzed by any effective means for identifying breast precancer or cancer, including e.g. cytological analysis of the cells retrieved or identified. Examination of the ductal epithelial cells can be accomplished by examining useful indicators such as, e.g. the morphology of the cells or the cellular contents. The cellular contents can include, e.g. protein, nucleic acid, particles, complexes or other biochemical or molecular markers in the cells. Cell morphology can serve to establish whether the ductal epithelial cells are normal (i.e. not precancerous or cancerous or having another non-cancerous abnormality), precancerous (i.e. comprising hyperplasia, atypical ductal hyperplasia (ADH) or low grade ductal carcinoma in situ (LG-DCIS)) or cancerous (i.e. comprising high grade ductal carcinoma in situ (HG-DCIS), or invasive carcinoma).

Analysis of cell contents may serve to establish similar staging as established by morphology, capturing generally a progression of a precancerous or cancerous condition in the cells. Thus the ductal epithelial cells may be analyzed for other markers, e.g. protein markers, nucleic acid markers, particles, complexes, or biochemical or molecular markers in the cells or on the cell surfaces or secreted by the cell or for any marker providing evidence of neoplasia. The ductal epithelial cell can be derived from any part of the breast milk duct, including, e.g. the ductal lumen and/or the terminal ductal lobular unit (TDLU). Cells derived from the TDLU may also have similar stages as found in other luminal ductal epithelial cells not from the TDLU including, e.g. hyperplasia, atypia, in situ carcinoma, and invasive carcinoma.

Once the wash fluid had been infused in the duct and the wash fluid and ductal fluid is collected from a breast duct, the cellular material can be separated and can be examined. The cellular material can include, e.g. substances selected from the group consisting of whole cells, cellular debris, proteins, nucleic acids, polypeptides, glycoproteins, lipids, fats, glycoproteins, small organic molecules, metabolites, and macromolecules. Cytology, or any other suitable method for analyzing the condition of the cells can examine whole cells. Other markers present in the cellular material, ductal fluid generally, or other material obtained from the breast duct can be analyzed as is appropriate for the marker being sought, including e.g. binding assays, immunohistochemistry, or using other analytical technology for distinguishing and identifying biological molecules obtained from biological material.

Identifying a patient having breast cancer or breast precancer can be accomplished by removing breast duct fluid from the patient and analyzing the fluid comprising ductal contents for markers that may indicate a cancerous or precancerous condition in the breast. Providing a ductal fluid sample from one duct of a breast of a patient includes that the fluid is not mixed with ductal fluid from any other duct of the breast. The method is practiced by providing a ductal fluid sample from at least one duct of a breast of the patient. Providing the ductal fluid sample can comprise obtaining the sample from the breast. Providing the ductal fluid sample can also comprise receiving a sample that had been previously obtained. For example, a laboratory can receive a ductal fluid sample from a patient or a practitioner, and the laboratory can be directed to make an analysis of the sample. Where the fluid is obtained from the breast, the fluid sample can be obtained e.g. by nipple aspiration of the milk ducts or by ductal lavage of at least one breast milk duct. When fluid is collected by nipple aspiration, or by ductal lavage, the fluid can be collected from a single duct. For example the duct and the collection tube can be marked so that the analysis of the fluid is traceable to one duct.

The ductal fluid can be retrieved by placing a ductal access tool in the duct and infusing fluid into the duct through the tool and retrieving from the accessed duct through the tool a portion of the infused fluid mixed with ductal fluid. The process may be repeated for more than one duct on a breast, and/or the process can be repeated for a plurality of ducts on a breast. Either sequential or simultaneous access of the duct on a breast can be used.

The next step in the method after the fluid is collected is examining the ductal fluid sample to determine the presence of a marker comprising a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules.

Examining the ductal fluid sample can comprise determining the presence of a marker comprising RNA, DNA, protein, polypeptide, or peptide form of a marker selected from the group consisting of a receptor, a ligand, a protein factor, an antigen, an antibody, an enzyme, a soluble protein, a cytosolic protein, a cytoplasmic protein, a tumor suppressor, a cell surface antigen, a phospholipid, a lipoprotein, a hormone responsive protein, a differentiation associated antigen, a proliferation associated antigen, a metastasis associated antigen, an integral membrane protein, a protein that participates in an apostasis pathway, a protein that participates in a transcriptional activation pathway, a cell adhesion molecule, an extracellular matrix protein, a proteolipid, a cytokine, a basement membrane protein, a mucin-type glycoprotein, a histone, a ribonucleoprotein, a sialic acid, a bone matrix protein, a carbohydrate antigen, a nuclear protein, a nuclear phosphoprotein, a proto-oncogene, an oncogene, an apolipoprotein, a serine protease, a tumor rejection antigen, a surfactant protein, a cell death protein, a zinc endoprotease, and a trefoil gene.

Examining the ductal fluid sample can comprise determining the presence of a marker comprising RNA, DNA, protein, polypeptide, or peptide form of a marker selected from the group consisting of a chemokine, a lectin, an integrin, a selectin, a keratin, an interleukin, a taxin, a ferritin, a lipocalin, a laminin, a cyclin, a relaxin, a nuclein, a caspase, a melanoma-associated antigen, a macrophage inflammatory protein, a gap junction protein, a calcium binding protein, an actin binding protein, a phospholipid binding protein, a heat shock protein, a cell cycle protein, an activator of tyrosine and tryptophan hydroxylase, a member of the tumor necrosis factor family of proteins, a member of the transforming growth factor alpha family of proteins, a member of the transforming growth factor beta family of proteins, a member of the Bcl2 family of proteins, a Bcl2-interacting protein, a Bcl2-associated protein, a member of the vasopressin/oxytocin family of proteins, and a member of the CCAAT/enhancer binding protein family of proteins.

Examining the ductal fluid sample can comprise determining the presence of a marker wherein the marker is an enzyme and the enzyme comprises an RNA, DNA, protein, polypeptide, or peptide form of an enzyme selected from the group consisting of a phosphorylase, a phosphatase, a decarboxylase, an isoenzyme, a kinase, a protease, a nuclease, a peptidase, a protease, a DNase, an RNase, an aminopeptidase, a topoisomerase, a phosphodiesterase, an aromatase, a cyclooxygenase, a hydroxylase, a dehydrogenase, a metalloproteinase, a telomerase, a reductase, a synthase, an elastase, a tyrosinase, a transferase, and a cyclase.

Examining the ductal fluid sample can comprise determining the presence of a marker wherein the marker is a receptor and the receptor comprises an RNA, DNA, protein, polypeptide, or peptide form of a receptor selected from the group consisting of a steroid hormone receptor, a growth factor receptor, a kinase receptor, a G-protein linked receptor, a TNF family receptor, a tyrosine kinase receptor, a vasopressin receptor, an oxytocin receptor, and a serine protease receptor.

Examining the ductal fluid sample can comprise determining the presence of a marker wherein the marker is a protein factor and the factor comprises an RNA, DNA, protein, polypeptide, or peptide form of a factor selected from the group consisting of a growth factor, a proteolytic factor, a stromal cell factor, an epithelial cell factor, an angiogenesis factor, an epithelial cell factor, an angiogenic factor, and a colony stimulating factor.

Examining the ductal fluid sample can comprise determining the presence of a marker wherein the marker is an inhibitor and the inhibitor comprises an RNA, DNA, protein, polypeptide, or peptide form of an inhibitor selected from the group consisting of an inhibitor of a cyclin, an inhibitor of a cyclin complex, a serpin, an inhibitor of proteolytic degradation, a tissue inhibitor of a metalloprotease, and an angiogenesis inhibitor.

Examining the ductal fluid can comprise identifying a level or quality of at least one marker comprising an expression product of a gene encoding a nuclear matrix protein.

A level of the marker can be a presence relative to a normal control or an absence relative to a normal control of a given marker. The normal control can be determined relative to the particular patient, or relative to a patient population.

In addition, the quality of the marker can be assessed. A quality of a marker can be such changes as DNA mutation, or a quantity of mutations, a deterioration of chromosomal quality or quantity, degradation of a protein, or a change in quantity of a nucleic acid or chromosome. A quality can be an erosion of a molecule, particle, molecule or organelle with respect to a normal quality.

Once the wash fluid had been infused in the duct and the wash fluid and ductal fluid is collected from a breast duct, the cellular material can be separated and can be examined. The cellular material can include, e.g. substances selected from the group consisting of whole cells, cellular debris, proteins, nucleic acids, polypeptides, glycoproteins, lipids, fats, glycoproteins, small organic molecules, metabolites, and macromolecules. Examining the ductal fluid sample to determine the presence of a marker comprising a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules. Detection and analysis of these classifications of markers can be accomplished as described below, using standard assays for determining the presence of markers or marker classifications listed, for example as described in Sambrook et al., Molecular Cloning: A Laboratory Manual, $2^{nd}$ Ed. (Cold Spring Harbor Press, Cold Spring Harbor, N.Y. 1989).

Cytology, or any other suitable method for analyzing the condition of the cells can examine whole cells. Other markers present in the cellular material, ductal fluid generally, or other material obtained from the breast duct can be analyzed as is appropriate for the marker being sought, including e.g. binding assays, immunohistochemistry, or using other analytical technology for distinguishing and identifying biological molecules obtained from biological material.

Intracellular components, either secreted or non-secreted and which are found in the ductal fluid may be tested as well. For example, ring-shaped particles which comprise protein, DNA, and RNA can be identified using an assay and/or a binding immogen as described in U.S. Pat. Nos. 5,635,605, and 5,459,035, and EP 465,715, including (as described) an affinity chromatography medium specific for proteins with particular characteristics (in the case of the ring-shaped particle a dinucleotide fold) and a standard immunoassay proceeding as described. In addition, complexes of proteins or other molecules may be identified. For example, antibodies may be used to bind complexes, e.g. extracellular matrix complexes in order to identify such a complex that is considered a breast cancer marker. The process of identification of such complexes is described in WO 96/12192.

Exemplary markers are described in Masood S., (Prediction of recurrence for advanced breast cancer. Traditional and contemporary pathologic and molecular markers) *Surgical Oncology Clinics of North America.* 4(4): 601–32, 1995; Lopez-Guerrero et al (1999) *J Hematother* 8(1):53–61; Marjumdar and Diamandis (1999) *Br J Cancer* 79(9–10):1594–602; Balleine et al (1999) *Br J Cancer* 79 (9–10):1564–71; Houston et al (1999) *Br J Cancer* 79(7–8): 1220–6; Nikolic-Vukosavljevic et al (1998) *Tumori* 84(6): 691–4; Maguire et al (1998) *Int J Biol Markers* 13(3): 139–44; Steams et al (1998) *Breast Cancer Res Treat* 52(1–3):239–59; Eiriksdottir et al (1998) *Eur J Cancer* 34(13):2076–81, and U.S. Pat. No. 5,169,774. Many known breast cancer markers are discussed and described in readily available medical textbooks on breast cancer. In addition, several markers can be identified and analyzed in the same sample, e.g. Fabian et al 1993 *J Cellular Biochemistry* 17G:153–16 and Fabian et al 1994 *Breast Cancer Res Treat*

30(3):263–74 looking at estrogen receptor (ER), epidermal growth factor receptor (EGFR), mutant p53, HER-2 neu by immunohistochemistry and aneuploidy by image analysis in fine needle aspirates. Methods described therein can be practiced by analogy to analysis of ductal fluid contents, particularly ductal epithelial cells retrieved by nipple aspiration and/or by ductal lavage techniques.

Chromosomal abnormalities in ductal epithelial cells can also provide information and act as a marker to identify cancer or precancer as described in Mark et al (1999) *Cancer Genet Cytogenet* 108:26–31; Lundlin and Mertens (1998) *Breast Cancer Res Treat* 51:1–15; Newsham (1998) *Am J Pathol* 153:5–9; Larson et al (1998) *Am J Pathol* 152:1591–8; Adelaide et al (1998) *Genes Chromosomes Cancer* 22:186–99; Fejzo et al (1998) *Gene Chromosome Cancer* 22:105–113; Dietrich et al (1998) *Hum Pathol* 12: 1379–82; Cavalli et al (1997) *Hereditas* 126:261–8; Adeyinka et al (1997) *Cancer Genet Cytogenet* 97:119–21; Afify and Mark (1997) *Cancer Genet Cytogenet* 97:101–5; Brenner and Aldaz (1997) *Prog Clin Biol Res* 396: 63–82; Mark et al (1997) *Ann Clin Lab Sci* 27:47–56; and Fabian et al 1993 *J. Cellular Biochemistry* 17G:153–16.

Other breast cancer markers can be detected as described in Springer, G. F. et al, Dao et al, Eds, *Tumor Markers and Their Significance in the Management of Breast Cancer*, pp.47–70, New York; A. R. Liss, 1986. In addition to some markers discussed and/or articles or books cited on breast cancer and breast precancer markers, including markers listed in Porter-Jordan and Lippman, "Overview of the biological markers of breast cancer", Hematology/Oncology Clinics of North America vol. 8 (1):73–100, 1994), the following cancer markers are listed here as exemplary and may be used as well as other markers to analyze the condition of a breast duct, including analysis of the ductal contents (including fluid and cells). Standard assay procedures for identifying the markers can be used, including antibodies or other binding partners, labels, stains, pattern analysis (for cells and cell components), and in general any other chemical or visual identification techniques.

Exemplary markers that are presently being studied by researchers directing their research to breast cancer include, for example, carcinoma embryonic antigen (CEA), prostate specific antigen (PSA) Erb B2 antigen, gross cystic disease fluid protein-15 (GCDFP-15), and lactose dehydrogenase (LDH). For CEA see Imayama et al, *Cancer* 1996, 78(6): 1229–34; Inaji et al, *Cancer* 1987,60(12):3008–13; Mori *Int Conger Seer* 1989, 807:211–8; Inaji, et al, *An To Kagaku Ryoho* 1991, 18(2):313–7; Yayoi, et al *Gan To Kagaku Ryoho* 1994, 21 Suppl 2:133–9; Mori, et al *Jpn J Clin Oncol* 1989,19(4):373–9; Foretova, et al *Proc Annu Meet Am Soc Clin Oncol* 1995,14:A101; and Nishiguchi, et al *Rinsho Byori* 1992,40(1):67–72. For PSA see Foretova and Garber *Lancet* 1996,347(9015):1631; Sauter et al, *Cancer Epidemiology, Biomarkers & Prevention.* 5(12):967–70, 1996; Sauter and Daly (1996) *Proc Annu Meet Am Assoc Cancer Res* 37:A1458; and Foretova and Garber (1996) *Proc Annu Meet Am Assoc Cancer Res* 37:A1446. For Erb B2 see Motomura (1995) *Breast Cancer Res and Treat* 33:89–92; and Inaji et al (1993) *Tumour Biol* 14:271–8. For GCDFP-15 see Petrakis et al (1994) *Proc Annu Meet Am Assoc Cancer Res* 35:A1698. For LDH see Mannello et al (1995) *Cancer* 76:152–4; and Kawamoto (1994) *Cancer* 73:1836–41.

Generally markers can be, for example, a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules. These markers can be detected by detecting an RNA, DNA, protein, polypeptide, or peptide form of a marker selected from the group consisting of, for example, a chemokine, a lectin, an integrin, a selectin, a keratin, an interleukin, a taxin, a ferritin, a lipocalin, a laminin, a cyclin, a relaxin, a nuclein, a caspase, a melanoma-associated antigen, a macrophage inflammatory protein, a gap junction protein, a calcium binding protein, an actin binding protein, a phospholipid binding protein, a heat shock protein, a cell cycle protein, an activator of tyrosine and tryptophan hydroxylase, a member of the tumor necrosis factor family of proteins, a member of the transforming growth factor alpha family of proteins, a member of the transforming growth factor beta family of proteins, a member of the Bcl2 family of proteins, a Bcl2-interacting protein, a Bcl2-associated protein, a member of the vasopressin/oxytocin family of proteins, and a member of the CCAAT/enhancer binding protein family of proteins; or selected from the group consisting of a chemokine, a lectin, an integrin, a selectin, a keratin, an interleukin, a taxin, a ferritin, a lipocalin, a laminin, a cyclin, a relaxin, a nuclein, a caspase, a melanoma-associated antigen, a macrophage inflammatory protein, a gap junction protein, a calcium binding protein, an actin binding protein, a phospholipid binding protein, a heat shock protein, a cell cycle protein, an activator of tyrosine and tryptophan hydroxylase, a member of the tumor necrosis factor family of proteins, a member of the transforming growth factor alpha family of proteins, a member of the transforming growth factor beta family of proteins, a member of the Bcl2 family of proteins, a Bcl2-interacting protein, a Bcl2-associated protein, a member of the vasopressin/oxytocin family of proteins, and a member of the CCAAT/enhancer binding protein family of proteins. An example of a peptide marker is fibrinogen degredation peptide, which can be assayed as described in WO 98/55872. Another marker that may be detected, e.g., by ELISA tests on the ductal fluid is called DR70™. DR70™ may be sought from ductal fluid essentially as described in Wu et al., *J. Immunoassay,* 1998 vol. 19; no. 1:63–72.

The marker may also or alternatively be an enzyme and the enzyme can comprise an RNA, DNA, protein, polypeptide, or peptide form of an enzyme such as for example, a phosphorylase, a phosphatase, a decarboxylase, an isoenzyme, a kinase, a protease, a nuclease, a peptidase, a protease, a DNase, an RNase, an aminopeptidase, a topoisomerase, a phosphodiesterase, an aromatase, a cyclooxygenase, a hydroxylase, a dehydrogenase, a metalloproteinase, a telomerase, a reductase, a synthase, an elastase, a tyrosinase, a transferase, or a cyclase.

The marker may also or alternatively be a receptor and the receptor can comprise an RNA, DNA, protein, polypeptide, or peptide form of a receptor such as for example a steroid hormone receptor, a growth factor receptor, a kinase receptor, a G-protein linked receptor, a TNF family receptor, a tyrosine kinase receptor, a vasopressin receptor, an oxytocin receptor, and a serine protease receptor.

The marker may also or alternatively be a protein factor and the protein factor can comprise an RNA, DNA, protein, polypeptide, or peptide form of a protein factor such as for example a growth factor, a proteolytic factor, a stromal cell factor, an epithelial cell factor, an angiogenesis factor, an epithelial cell factor, an angiogenic factor, or a colony stimulating factor.

The marker may also or alternatively be an inhibitor and the inhibitor can comprise an RNA, DNA, protein, polypeptide, or peptide form of an inhibitor such as for example an inhibitor of a cyclin, an inhibitor of a cyclin complex, a serpin, an inhibitor of proteolytic degradation, a tissue inhibitor of a metalloprotease, and an angiogenesis inhibitor.

The different categories of markers are tested differently depending on the category and possibly also on the location of the marker in the cell (for example, a cell surface protein might be detected differently than a cytoplasmic or nuclear protein). Typically, assays comprising one or more of binding, coloration, precipitation, affinity column selection, in-situ binding, solution phase binding, nucleic acid probe labeling, protein probe labeling, polypeptide probe labeling, peptide probe labeling, and/or a combination or variation of these processes can be used. Standard procedure for conducting such assays generally (e.g. ELISA, RNA or DNA probe hybridization, and other binding or other detection assays) are described in Sambrook et al., Molecular Cloning: A Laboratory Manual, $2^{nd}$ Ed. (Cold Spring Harbor Press, Cold Spring Harbor, N.Y. 1989).

More specifically, examples of detection of particular markers or classes of markers are described in Table I below that lists exemplary markers and cites references in which those markers are detected. For markers not specifically listed, broad categories such as e.g. proteins, lipids, RNA transcripts, glycoproteins, and other categories can be detected for other specific markers in the same fashion as specific markers in a same or similar category. Some of these specific markers belonging to broader categories are listed in Table I.

In addition to some markers discussed and/or articles or books cited on breast cancer and breast precancer markers, the following cancer markers are listed here as exemplary and may be used as well as other markers to analyze the condition of a breast duct. Standard assay procedures for identifying the markers can be used, including antibodies or other binding partners, labels, stains, pattern analysis (for cells and cell components), and in general any other chemical or visual identification techniques.

The following are exemplary potential markers for such identification and analysis: cathepsins (including cathepsin D); maspin, fas, fas ligand, tissue inhibitor of matrix metalloproteinas-1 (TIMP-1); chemokines (both C-C and C-X-C type chemokines); collagenases, metalloproteinases, TIMP's, cathepsins, disrupted basement membrane epitopes, stromolysin-3; cytokeratins (e.g. keratin 14, B1, KA1, KA4 and 312C8–1); estrogen and progesterone receptors (or any androgen or other steroid receptor); growth factor receptors for members of the fibroblast growth family (FGF) including FGF1–18, vascular endothelial growth factor (VEGF), insulin-like growth factor-1 (IGF-I), IGF-II, platelet-derived growth factor (PDGF), keratinocyte growth factor (KGF), and epithelial growth factor (EGF); placental growth factor (PLGF), hepatocyte growth factor (HGF), tumor necrosis factor (TNF), transforming growth factor (TGF) both alpha and beta forms, and angiopoietin, for example; heat shock proteins (HSP) (e.g. HSP27) 27 (HSP27); ErB type 1 tyrosine kinase receptors (e.g. Her2 (an EGF receptor) or any ligand or receptor of the ErbB family of ligands and receptors); integrins, selectins, cadherins, for example (i.e. alpha and beta 3 integrin); keratin-14; known cancer antigens including, for example Ki-67, Ki-S1, p53, nm23, bcl-2, p21 ras, cyclins, and pS2; thrombin receptor activating peptide; urokinase, urokinase-type plasminogen activator (UPA), plasmin antiplasmin; UPA receptor (UPAR), fibrinogen, plasmin activator inhibitor-1 and 2 (PAI-1 and 2); telomerase; antibodies to tumor associated antigen-72 (TAG-72) (e.g. B72.3, B6.2, and TKH2); carcinoembryonic antigen (CEA) (see e.g. EP 319,686); prostate specific antigen (PSA); gross cystic disease fluid protein-15 (GCDFP-15); lactose dehydrogenase (LDH); chromosomal abnormalities (e.g. aneuploidy or other abnormalities); S1 protein; alkaline phosphatase; myosin; sialyl Tn (STn) glycopeptide (e.g. TAG-72); Tn glycopeptide; and nuclear matrix proteins (as described in provisional patent application Ser. No. 60/166,100 filed Nov. 17, 1999, herein incorporated by reference in its entirety).

Other breast cancer markers include, e.g. alanine aminopeptidase, alpha 6 integrin, alpha-lactalbumin, AN43 antigen (BB1), annexin 1, anti-Her2, anti-p53, Bad, BAG-1, Bak, Bax, BCA225, Bcl-2, Bcl-x, beta 1–6 branched oligosaccharides, beta-2 microglobulin (BMG), Bfl-1, bone sialoprotein (BSP), C/EBP beta-LIP, Ca 1 antigen, CA27.29, CA M26, CA M29, CA125, CA15.3, CA195, CA19-9, CA50, CA549, Cadherin-11, calcitonin receptor (CTR), cathepsin B, cathepsin L, CD 105, CD24, CD34 (pan-endothelial marker), CD44, CEA, c-met, c-myc, Cox-1, Cox-2, CPP32, cyclic nucleotide phosphodiesterase, cyclin E, DNA topoisomerase II-alpha, DNA topoisomerase II-beta, EGF, EGFR, E-selectin, fast homoarginine-sensitive alkaline phosphatase (FHAP), fatty acid synthase, ferritin, GCDFP-15/BRST-2, Her-2 (extracellular), h-mts1 (S100A4), hsc73, hsp70, hsp90alpha, hsp90beta, ID1, ID3, interleukin-1 beta, keratin 8, keratin 18, keratin 19, laminin, laminin receptor (MluC5), leucine aminopeptidase (LAP), lipid-bound sialic acid (LSA), MAGE-1, MAGE-2, MAGE-3, Man6-P glycoproteins, MCA, Mcl-1, metallothionein (MT), MKP-1, MMP-2, MMP-9, MSA, MUC-2, MUC-3, MUC-6, Nm23, ornithine decarboxylase (ODC), osteopontin (OPN), P114 (MAR binding protein), P120 (a nucleolar proliferation antigen), p125FAK, p330d/CENP-F (a marker for cell proliferation), PAI-2, Pepsinogen C, placental alkaline phosphatase (PLAP), platelet factor 4 (angiogenic marker), protein kinase C (PKC), PSA, pyrimidine nucleoside phosphorylase, ras p21, reduced glutathione (GSH), retinoid X receptor alpha, ribosomal S2 protein, sialyltransferase, Stromelysin-1 (MMP-3), surfactant proteins A, surfactant proteins B, TAG-12, TFF-1, TFF-3 (also called ITF, hP1.B and is another trefoil protein besides pS2), thrombin, thrombomodulin, thymidine phosphorylase (TP), thymosin beta 15, tissue cytosol ferritins, tissue polypeptide antigen (TPA), TPS (antigen for M3 antibody), uPAI, VEGF-B, VEGF-C, VEGF-R1, VEGF-R2, and VEGF-R3.

In general, markers can be categorized nonexclusively, and often in overlapping categories as follows: 1. Markers that are detected or detectable by virtue of protein expression or overexpression (detection may occur, e.g. by immunohistochemistry or in situ hybridization); 2. Markers that are detected or detectable by virtue of mRNA expression or overexpression (detection may occur, e.g. by differential display techniques); 3. Markers that are detected or detectable by virtue of a post translational change in a protein, e.g. a phosphorylation of the protein, a ubiquitination, a farnesylation, methylation, or other modification to the protein that can be detected, e.g. by antibodies specific to the post translational modification; and 4. Markers may also be detected based on alteration of a gene, for example methylation of the gene, for example, methylation of the retinoic acid receptor beta-2 gene (RARbeta-2), as described in Widschwenedter et al., *J. Natl Cancer Inst.* 2000 92 (10): 826–32.

Genes that are overexpressed in breast cancer and can be found by differential display include, e.g. Claudin-7, zinc-alpha-2-glycoprotein, apolipoprotein B, B94, EST (R08988), thrombospondin (THBS1), FGF-1, NGAL-Lipocalin 2, EST (N77731), BS247 (Abbott labs WO 99/22027), AIB-1. Genes that are identifiable by tyrosine phosphorylation changes include, e.g. Erb-B2 and EGFR. Genes that are identifiable by gene methylation include e.g. 14-3-3, SPR1, cyclin D2, GST-pi, and estrogen. Markers that are absent in tumors and are thus termed tumor suppressor markers and when absent or lower than normal levels indicate a tumorogenic condition, include, e.g. mammastatin, maspin, retinoic acid receptor-beta 2, and BRMS1 (a metastasis-suppressor gene). See, Cancer Res 2000 60: 2764–2769.

Accordingly, markers such as the following can sought in ductal fluid, e.g. proteins that are overexpressed, mRNA transcripts that are over expressed, and proteins comprising post translational modifications. For example, the following markers can be identified to distinguish a cancer or precancer cell from a normal cell. Proteins that are overexpressed can include e.g. Stromelysin-3, Membrane Type 1 Matrix Metalloproteinase (MT1-MMP), Matrix Metalloproteinase-3 (MMP-3), Placental Isoferrintin (p43), Nuclear Matrix Protein (NMP22), NM-200.4 specific antigen, Vascular Endothelial Growth Factor (VEGF), Endoglin (CD105), Telomerase, ErbB-2, ErbB-3, Carcinoembryonic Antigen (CEA), Heat Shock protein-27 (HSP-27), Breast Cancer-specific Gene (BCSG), Plasminogen Activator Inhibitor (PAI-1), Urokinase Plasminogen Activator (uPA), Urokinase Plasminogen Activator Receptor (uPAR), Colony Stimulating Factor-1 (CSF-1), Colony Stimulating Factor-1 receptor (fins), Annexin I, Vasopressin, the CC Chemokine Regulated on Activation Normal T cell Expressed and Secreted (RANTES), 44-3A6 specific antigen, A-80 specific antigen, MUC-1, H23 specific antigen, 83 D4 specific antigen, SP-2 specific antigen, 323/A3 specific antigen, tumor associated antigen-72 (TAG-72), and MBE6 specific antigen.

Other breast cancer markers detected by any means including e.g. protein expression, mRNA expression, or post translational modification can include e.g. (listed alphabetically) alanine aminopeptidase, alpha 6 integrin, alpha-lactalbumin, AN43, p53, Bcl2-antagonist of cell death (Bad), Bcl2-associated athanogene (BAG-1), Bcl2-antagonist/killer 1 (Bak), Bcl2-associated X protein (Bax), Breast cancer antigen 225 (BCA225), B-cell CLL/lymphoma 2 (Bcl-2), Bcl2-like 1 (Bcl-x), beta 1–6 branched oligosaccharides, beta-2 microglobulin (BMG), Bcl2 related protein A1 (Bfl-1), bone sialoprotein (BSP), CCAAT/enhancer-binding protein liver-enriched inhibitory protein (C/EBPbeta-LIP), Carcinoma Antigen 1 (Ca 1), Carcinoma Antigen 27.29 (CA 27.29), Carcinoma Antigen M26 (CA M26), Carcinoma Antigen M29 (CA M29), Carcinoma Antigen 125 (CA125), Carcinoma Antigen 15.3 (CA15.3), Carcinoma Antigen 195 (CA195), Carcinoma Antigen 19-9 (CA19-9), Carcinoma Antigen 50 (CA50), Carcinoma Antigen 549 (CA549), Cadherin-11, calcitonin receptor (CTR), cathepsin B, cathepsin L, Endoglin (CD105), CD24, CD34 (pan-endothelial marker), CD44, c-met/hepatocyte growth factor receptor, c-myc, cyclooxygenase-1 (Cox-1), cyclooxygenase-2 (Cox-2), caspase-3 (CPP32), Cyclic nucleotide phosphodiesterase, cyclin E, DNA topoisomerase II-alpha, DNA topoisomerase II-beta, EGF, EGF receptor, E-selectin, fast homoarginine-sensitive alkaline phosphatase (FHAP), fatty acid synthase, ferritin, gross cystic disease fluid protein (GCDFP-15/BRST-2), metastasis-associated h-mts1 (S100A4), heat shock cognate protein-73 (hsc73), heat shock protein-70 (hsp70), heat shock protein-90 alpha (hsp90alpha), heat shock protein-90 beta (hsp90beta), inhibitors of differentiation-1 (ID1), inhibitors of differentiation-3 (ID3), interleukin-1 beta, Keratin 8, Keratin 18, Keratin 19, Laminin, Laminin receptor (MLuC5), Leucine Aminopeptidase (LAP), lipid-bound sialic acid (LSA), Melanoma antigen-1 (MAGE-1), Melanoma antigen-2 (MAGE-2), Melanoma antigen-3 (MAGE-3), Man6-P glycoproteins, Mucin-like carcinoma associated antigen (MCA), myeloid cell leukemia-1 (Mcl-1), metallothionein (MT), mitogen-activated protein kinase phosphatase-1 (MKP-1), Matrix Metalloproteinase-2 (MMP-2), Matrix Metalloproteinase-9 (MMP-9), mammary serum antigen (MSA), breast cancer mucin-2 (MUC-2), breast cancer mucin-3 (MUC-3), breast cancer mucin-6 (MUC-6), Nm23 nucleoside diphosphate kinase, ornithine decarboxylase (ODC), osteopontin (OPN), P114 (MAR binding protein), P120 (a nucleolar proliferation antigen), focal adhesion kinase p125FAK, nuclear autoantigen p330d/CENP-F, plasminogen activator inhibitor-2 (PAI-2), Pepsinogen C, placental alkaline phosphatase (PLAP), Platelet factor 4 (angiogenic marker), protein kinase C (PKC), prostate specific antigen (PSA), pyrimidine nucleoside phosphorylase, ras p21, reduced glutathione (GSH), retinoid X receptor alpha, ribosomal S2 protein, sialyltransferase, Stromelysin-1 (MMP-3), surfactant proteins A, surfactant proteins B, tumor associated antigen-12 (TAG-12), trefoil gene TFF1, trefoil gene TFF3/ITF/hP1.B, Thrombin, Thrombomodulin, thymidine phosphorylase (TP), thymosin beta 15, tissue cytosol ferritins, tissue polypeptide antigen (TPA), tissue polypeptide specific antigen (TPS), Vascular Endothelial Growth Factor-B (VEGF-B), Vascular Endothelial Growth Factor-C (VEGF-C), Vascular Endothelial Growth Factor receptor-1(VEGFR1), Vascular Endothelial Growth Factor receptor-2 (VEGFR2), and Vascular Endothelial Growth Factor receptor-3 (VEGFR3).

With respect specifically to nuclear matrix proteins the process is similar as for other markers: the ductal fluid can be examined to determine the presence of a marker comprising an expression product of a gene encoding a nuclear matrix protein. The expression product can comprise a nucleic acid or a polypeptide. The expression product can comprises an RNA. The expression product can comprise a protein or a part of a protein. The nuclear matrix protein can be selected from the group consisting of lamin A, lamin B, lamin C, a peripheral matrix protein, nuclear mitotic spindle apparatus protein (NuMA), topoisomerase II, and an internal nuclear matrix protein. The expression product can be a polypeptide and examining the polypeptide can comprise contacting the polypeptide marker with an antibody that specifically binds a portion of the polypeptide.

The expression product can be a nucleic acid and examining it can comprise detecting the presence of the nucleic acid. Detecting the presence of the nucleic acid can comprise amplifying the nucleic acid, e.g. by PCR. For example, the ductal fluid can be tested for the presence of NMP66, a nuclear matrix protein specific for breast cancer. The advantage of testing for NMP molecules by retrieval of ductal fluid is that the sensitivity is increased, and the likelihood of early detection of ductal carcinoma in situ is increased by measuring a local concentration of the marker and not a concentration derived from the whole body. This advantage is also aided by the opportunity that ductal fluid and cell retrieval via a known and identified duct provides the opportunity to treat the duct or ductal system and not necessarily the breast. This may be important especially where precancer (such as ductal carcinoma in situ) is detected, and such detection does not necessarily warrant either a systemic treatment, nor a treatment directed to active, invasive cancer. Detection of breast cancer specific NMPs is described, e.g., in U.S. Pat. No. 5,914,238.

Once the ductal fluid is located or isolated, the fluid can be tested for the presence of one or more expression products of genes encoding nuclear matrix proteins (e.g. either an RNA or a polypeptide) in order to evaluate a presence of cancerous or precancerous cells in the duct. Such tests can typically be antibody or nucleic acid amplification tests that are commonly performed in the art of marker detection. The gene products identified can be any nuclear matrix protein gene product, including nuclear matrix gene products specific to malignancy in the breast, and possibly including e.g. lamin A, lamin B, lamin C, a peripheral matrix protein, nuclear mitotic spindle apparatus protein (NuMA), topoisomerase II, or an internal nuclear matrix protein. Assays, kits and methods described in U.S. Pat. Nos. 5,965,376, 5,914,238, 5,882,876, 5,858,683, 5,840,503, 5,830,677, 5,783,403, 5,780,596, 5,698,439, 5,686,562, or 5,547,928 can be adapted and applied to testing ductal fluid samples.

Once the ductal fluid is analyzed for one or more markers, the fluid may also be analyzed cytologically to determine the cytological status of the ductal epithelial cells and other cells. Cytological assays that can be performed on the cells retrieved from a duct or from nipple aspirate can include e.g. assays described in King et al, *J. Nat'l Cancer Inst* (1983) 71:1115–21, Wrensch et al. (1992) *Am. J. Epidem.* 135: 130–141, Papanicolaou et al, (1958) *Cancer,* 11:377–409 and Goodson W H & King E B, Chapter 4: *Discharges and Secretions of the Nipple,* The Breast: Comprehensive Management of Benign and Malignant Diseases (1998) $2^{nd}$ Ed. vol 2, Bland & Kirby eds. W.B. Saunders Co, Philadelphia, Pa. pp. 51–74. For example, as described in Goodson and King (page 60) atypical hyperplasia presents as having cellular abnormalities, increased coarseness of the chromatin, and tendency for more single cells as well as groups of cells. With regard to carcinoma in situ, Papanicolaou et al, described cellular abnormalities, e.g. nuclear abnormalities diagnosed by cytology of fluid from nipple secretions containing ductal cells. The cytology of abnormal cells can also be conducted as described in Sartorius et al (1977) *J. Natl Cancer Inst* 59: 1073–1080, and King et al, (1983) *JNCI* 71(6) 1115–1121. Atypia and carcinoma in situ are widely characterized pathologically, as described in Page et al, (1998) *Mod Pathol* 11(2): 120–8. The ductal fluid can be analyzed by cytological techniques by placing some of the fluid on a slide with a standard cytological stain using a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline T S and I K, Pub Igaku-Shoin Medical "Breast: Guides to Clinical Aspiration Biopsy" (LSBN 0896401596; Masood, *American Society of Clinical Pathology:* November 1995, "Cytopathology of the Breast" ISBN 0891893806; and Feldman P S, *American Society of Clinical Pathology,* November 1984, "Fine Needle Aspiration Cytology and Its Clinical Applications: Breast and Lung" ISBN 0891891846.

Other references that discuss cytological analysis and which give guidance to an analysis of ductal epithelial cells derived from ductal fluid include Silverman et al, (Can FNA biopsy separate atypical hyperplasia, carcinoma in situ, and invasive carcinoma of the breast?: Cytomorphologic criteria and limitations in diagnosis, Diagnostic Cytopathology) 9(6):713–28, 1993; Masood et al, (Immunohistochemical differentiation of atypical hyperplasia vs. carcinoma in situ of the breast) *Cancer Detection & Prevention.* 16(4): 225–35, 1992; Masood et al, (Cytologic differentiation between proliferative and nonproliferative breast disease in mammographically guided fine-needle aspirates) *Diagnostic Cytopathology.* 7(6):581–90, 1991; Masood S., (Occult breast lesions and aspiration biopsy: a new challenge) Diagnostic Cytopathology. 9(6):613–4, 1993; Masood S., (Prognostic factors in breast cancer: use of cytologic preparations) *Diagnostic Cytopathology.* 13(5):388–95, 1995; Novak and Masood, (Nuclear grooves in fine-needle aspiration biopsies of breast lesions: do they have any significance?) *Diagnostic Cytopathology.* 18(5):333–7, 1998; Sidawy et al, (Interobserver variability in the classification of proliferative breast lesions by fine-needle aspiration: results of the Papanicolaou Society of Cytopathology Study) *Diagnostic Cytopathology.* 18(2):150–65, 1998; Masood et al, (Automation in cytology: a survey conducted by the New Technology Task Force, Papanicolaou Society of Cytopathology) *Diagnostic Cytopathology.* 18(1):47–55, 1998; and Frykberg and Masood Copeland E M 3d. Bland K I., (Ductal carcinoma in situ of the breast) *Surgery, Gynecology & Obstetrics* 177(4):425–40, 1993.

As discussed, the cells collected can comprise ductal epithelial cells and the ductal fluid collected can comprise molecular and cellular material. The collected cells and fluid and fluid components can be analyzed, e.g. as described or suggested herein. Fluid collected from the milk ducts, can include constituents of biological fluids, e.g. those typically found in breast duct fluid, e.g. water, cells, cellular markers, molecular markers, nucleic acids, proteins, cellular debris, salts, particles or organic molecules. These constituents can be analyzed by any appropriate method depending on the marker and the diagnostic purpose. In addition, any of the cells of the duct can be analyzed for morphological abnormalities in cell components, including, e.g. morphological abnormalities of the nucleus, cytoplasm, Golgi apparatus or other parts of a cell. Cell morphology can serve to establish whether the ductal epithelial cells are normal (i.e. not precancerous or cancerous or having another noncancerous abnormality), precancerous (i.e. comprising hyperplasia, atypical ductal hyperplasia (ADH) or low grade ductal carcinoma in situ (LG-DCIS)) or cancerous (i.e. comprising high grade ductal carcinoma in situ (HG-DCIS), or invasive carcinoma). Analysis of cell contents may serve to establish similar staging as established by morphology, capturing generally a progression of a precancerous or cancerous condition in the cells.

Once the ductal fluid sample is retrieved from the breast it is examined for the presence of a marker such as, for example a protein, a polypeptide, a peptide, a nucleic acid, a polynucleotide, an mRNA, a small organic molecule, a lipid, a fat, a glycoprotein, a glycopeptide, a carbohydrate, an oligosaccharide, and a chromosomal abnormality, a whole cell having a marker molecule, a particle, a secreted molecule, an intracellular molecule, and a complex of a plurality of molecules as described above. In addition, the marker may be capable of differentiating between any two of cytological categories consisting of normal, abnormal, hyperplasia, atypia, ductal carcinoma, ductal carcinoma in situ (DCIS), ductal carcinoma in situ—low grade (DCIS-LG), ductal carcinoma in situ—high grade (DCIS-HG), invasive carcinoma, atypical mild changes, atypical marked changes, atypical ductal hyperplasia (ADH), insufficient cellular material for diagnosis, and sufficient cellular material for diagnosis. These categories classify the epithelial cells cytologically, and these classifications may indicate either cancer or its precursors, or absence of cancer indicia. The marker may be capable of differentiating between any two of cytological categories consisting of normal, abnormal, hyperplasia, atypia, ductal carcinoma, ductal carcinoma in situ (DCIS), ductal carcinoma in situ—low grade (DCIS-LG), ductal carcinoma in situ—high grade (DCIS-HG), invasive carcinoma, atypical mild changes, atypical marked changes, atypical ductal hyperplasia (ADH), insufficient cellular material for diagnosis, and sufficient cellular material for diagnosis.

For example, the number of epithelial cells in ductal lavage samples may range from none to several thousand. At least ten epithelial cells are required to designate a sample as adequate. Benign duct cells may be present singly, in monolayer sheets, or in tight clusters, using one to two cell layers thick. The cells are small with small nuclei (in a range from about 8 to about 12 μm in diameter). The nuclear to cytoplasmic ration may appear to be high depending on the orientation of the cells in clusters. Single benign duct cells are often difficult to identify, often appearing similar to surrounding lymphocytes or histiocytes. Duct cells may be recognized by the columnar shape of their cytoplasm, or by the presence of discreet small vacuoles in the cytoplasm. The smooth, discrete cytoplasmic border may also help to distinguish duct cells. Benign duct cells are more easily recognized when they occur in groupings. Cohesive groups, as opposed to looser clusters, are more suggestive of epithelial origin. Benign groups are one or two cell layers in thickness, and are composed of cells which are uniform in size. The cell nuclei are also uniform in size, and are regularly round to oval in shape. Markers that may be identified in addition to cytological notations, may assist a diagnosis by confirming a cytological reading and or adding additional information to any noteworthy subcategory within the category of benign.

The cytological category including atypical epithelial cells, with mild changes, includes duct cells from proliferative conditions including hyperplasia. The cells may occur singly, in cohesive multilayered and complex groups, and in monolayers. The groups may show an increase in the number of cell layers, which can be appreciated by focusing through the groups. Duct groupings also may show increased overlap, with nuclear crowding. The cells may be minimally enlarged, and may show moderate increases in nuclear size, in a range from 12 to 16 μm in diameter. Slight anisonucleosis may be present among cells in groups. Nucleoli are often present. Markers found in the ductal fluid may assist to identify atypical cells or atypical cells with mild changes, or may confirm such cytological identification.

Atypical cells can also include atypical cells with marked changes. More marked changes are often associated with atypical hyperplasia and low grade ductal carcinoma in situ (DCIS). Enlarged duct cells may be present, showing more marked nuclear increase and variation in size and shape. Single cells are enlarged, with the cytoplasm in some cases abundant, nuclear-to-cytoplasmic rations may actually appear decreased. Chromatin may appear coarse, with mild abnormality in distribution. Nucleoli may be larger, multiple, and more prominent. Nuclei in groups may appear to be overlapping. Mitotic figures may be seen. Markers found in the ductal fluid may assist to identify atypical cells with marked changes, or may confirm such cytological identification.

Malignant epithelial cells include duct cells from high grade breast carcinoma and exhibit common features of malignancy. More single cells are present, as cell cohesiveness is lost. Loose clusters of epithelial cells are present, along with the more usual tight groups of cells. Cell and nuclear enlargement may be marked. High nuclear to cytoplasmic ratios may be present in some cases. However, some high grade specimens often have lots of cytoplasm in a portion of the tumor cells, resulting in low or variable nuclear-to-cytoplasmic ratios. Nuclear membranes are often irregular, and chromatin is clumped, hyperchromatic, and unevenly dispersed. Nucleoli are often large and conspicuous and may be multiple. Marked variation among the cells can be seen in terms of cell and nuclear size. Accompanying these changes is often a background of necrotic debris. Microcalcifications may be seen in the background material. These may appear as dense material with smooth borders and concentric layers, or may be dystrophic, amorphous in nature. Markers found in the ductal fluid may assist to identify malignant cells, aspects of malignant indicia, or may confirm such cytological identification. Markers may also help to stage the malignancy or provide other valuable information which might aid in directing a detailed diagnosis and/or viable treatment options.

Other cytological criteria and processes related to ductal fluid analysis are described in Barret et al, Acta Cytol 1976;20:174–180; Goodson et al, Discharges and Secretions of the Nipple, The BREAST: COMPREHENSIVE MANAGEMENT OF BENIGN AND MALIGNANT DISEASES, Second Edition, Vol. 1, Chapter 4, page 1; King et al, Cytometry 1984; 5: 124–130; King et al, A.J.C.P. 1975; 64: 739–748; King et al, A.J.C.P. 1975; 64: 728–738; King et al, Cytopathology of Abnormal Mammary Duct Epithelium, Prevention and Detection of Cancer, Part II, Detection, vol 2 Cancer detection in specific sites, 1976; King et al, J Natl Cancer Inst, 1983; 71: 1115–1121; Kjellgren et al, Acta Cytol 1964; 8: 216–217; Masood et al, The Breast Journal 1999; 5:1–2; Papanicolaou et al, Cancer 1958; 377–409; Petrakis et al, Cancer Epidemiology, Biomarkers and Prevention 1993; 2:3–10; Ringrose et al, Acta Cytol 1966; 10:373–375; Sartorius et al, NCI 1977; 59:1073–1080; Sauter et al, British J. Cancer 1997; 76(4):494–501; Wrensch et al, Amer J. Epid. 1992; 135: 130–141.

The invention also provides systems for diagnosing breast cancer or precancer comprising a tool to retrieve ductal fluid from a breast duct and instructions for use to determine the presence of a marker identified. The systems can comprise kits which include a ductal access tool, for example in order to retrieve the ductal fluid, e.g. especially where it is preferred that the ductal fluid be identified as coming from a particular duct (so that the duct can be accessed later for treatment or further monitoring). The instructions in the kits can include directions according to the methods of identifying breast cancer or precancer described herein, and including any marker or markers or marker classification group or groups that are described herein. The kit or system can include assay reagents for detecting the marker or markers. The kit may comprise a panel for testing a plurality of markers either simultaneously or sequentially, or some practical combination of testing modalities. The kit can also include indexes and parameters for making a diagnosis, depending on the marker or markers. The kit can include a container for the kit contents.

The following table supplies some exemplary markers and marker categories and publications that identify particular identification methods for that category of marker and/or for the specific marker as well.

TABLE I

| # | CATEGORY | SPECIFIC EXAMPLES | NOTES (further description; marker forms and identification contexts; assays) |
|---|---|---|---|
| 1 | Integral membrane protein | Claudin (e.g. claudins 1, 2, or 3) | Kubota et al, Curr Biol. 1999; 9(18): 1035–8<br>Furuse et al, J Cell Biol. 1998; 141(7): 1539–50 |
| 2 | Glycoprotein<br>Hormone responsive protein<br>Cytosolic protein | Zinc-alpha-2-glycoprotein | Lopez-Boado et al, Breast Cancer Res. Treat 1994; 29(3): 247–58<br>Diez-Itza et al, Eur. J. Cancer 1993; 29A(9): 1256–60<br>Chaubert and Hurlimann, Arch Pathol Lab Med 1992; 116(11): 1181–8 |
| 3 | Aspartyl proteinase<br>Differentiation associated protein | Gross cystic disease fluid protein-15 kD (GCDFP-15) | Chaubert and Hurlimann, Arch Pathol Lab Med 1992; 116(11): 1181–8<br>Caputo et al, J Biol Chem, 2000; 275(11): 7935–41 |
| 4 | Lipoprotein | Apolipoprotein | Lane et al, Breast Cancer Res Treat 1995; 34(2): 161–9 |
| 5 | Peptide | CD36-binding peptide | Carron et al, Biochem Biophys Res Comm 2000 270(3): 1124–1127 |
| 6 | Ligand<br>Extracellular matrix protein | Thrombospondin-1 | Carron et al, Biochem Biophys Res Comm 2000 270(3): 1124–1127<br>Murphy-Ullrich and Poczatek, Cytokine Growth Factor Rev 2000; 11(1–2): 59–69 |
| 7 | Growth factor | Fibroblast growth factor | Fernig et al, Biochem Biophys Res Comm 2000; 267(3): 70–6 |
| 8 | Lipocalin | Neu-related lipocalin/neutophil gelatinase-associated lipocalin (NRL/NGAL) | Zerega et al, Eur J Cell Biol 2000; 79(3): 165–72 |
| 9 | Hormone responsive protein | Amplified in breast cancer-1 (AIB-1) | Eng et al, J Biol Chem 1998; 273(43): 28371–7 |
| 10 | Hormone responsive protein | Transcriptional intermediary factor -1 and -2 (TIF-1 & -2) | Eng et al, J Biol Chem 1998; 273(43): 28371–7 |
| 11 | Transferase | Glutathione S-transferase pi (GST-pi) | Huang et al, Oncol Rep 2000; 7(3): 609–13 |
| 12 | Differentiation associated protein | SPR-1 | Anisowicz et al, Mol Med 1999; 5(8): 526–41 |
| 13 | Differentiation associated protein<br>Activator of tyrosine and tryptophan hydroxylase | HME-1 (25 kd)<br>14-3-3 sigma protein<br>stratifin | Prasad et al, Cell Growth Differ 1992; 3(8): 507–13<br>U.S. Pat. No. 5,776,676 (nucleic acid)<br>U.S. Pat. No. 4,707,438 (immunoassay)<br>Isobe et al, J. Mol Biol 1991 217(1): 125–32<br>U.S. Pat. No. 5,597,719 (Raf interaction)<br>U.S. Pat. No. 5,424,191 (polypeptide)<br>14-3-3 sigma accession no.: AFO29082<br>Laronga et al, J Biol Chem, 2000: April 14 (no page numbers available) |
| 14 | Proto-oncogene<br>Cyclin | Cyclin D1 | Bukholm et al, Virchows Arch 1998; 433(3): 223–8<br>Sweeney et al, Oncogene 1997; 14(11): 1329–40<br>Buckley et al, Oncogene 1993: 8(8): 2127–33<br>Weinstat-Saslow et al, Nat Med 1995; 1(12): 1257–60<br>Barnes and Gillett, Breast Cancer Res Treat 1998; 52(1–3): 1–15<br>Reed et al, Virchows Arch 1999; 435(2); 116–24 |
| 15 | Growth factor | Vascular endothelial growth factor (VEGF)<br>Vascular permiability factor (VPF) | Toi et al, Clinical Cancer Res. 1995; 1: 961–964<br>Lichtenbeld et al, Int J Cancer 1998; 77(3): 445–9<br>Guidi et al, Cancer 1997; 80(10): 1945–53<br>Locopo et al, Breast Cancer Res Treat 1998; 52(1–3): 159–73<br>Wright et al, Exp Mol Pathol 1997; 64(1): 41–51<br>Yoshiji et al, Cancer Res 1996; 56(9); 2013–6<br>Brown et al, Human Pathol 1995; 26(1): 86–91 |
| 16 | Receptor | Vascular endothelial growth factor receptor (VEGF-R) flt-1 | Yoshiji et al, Cancer Res 1996; 56(9); 2013–6 |
| 17 | Proteolytic factor | Cathepsins D and L | Harbeck et al, Int J Markers 2000 15(1): 79–83<br>Ioachim et al, Anticancer Res 1998; 18(3A): 1665–70 |
| 18 | Tumor suppressor<br>Angiogenesis inhibitor | Maspin | Domann et al, Int J Cancer 2000; 85(6): 805–10<br>U.S. Pat. No. 5,470,970<br>Zou et al, J Biol Science, 2000; 275(9): 6051–4<br>Zhang et al, Nat Med 2000; 6(2): 196–9 |
| 19 | Receptor<br>Tumor necrosis family<br>Apoptosis pathway protein<br>Cell death protein | Fas<br>Apo-1<br>CD95 | Mottolese et al, Int J Cancer 2000 89(2): 127–32<br>Reimer et al, Cancer Res 2000; 60(4): 822–8 |
| 20 | Ligand<br>Tumor necrosis family<br>Apoptosis pathway protein<br>Cell death protein | Fas ligand (fasL) | Mottolese et al, Int J Cancer 2000 89(2): 127–32<br>Reimer et al, Cancer Res 2000; 60(4): 822–8 |
| 21 | Inhibitor | Tissue inhibitor of metalloproteinase 1 and 2 (TIMP-1, TIMP-2) | Brummer et al, Virchows Arch 1999; 435(6): 566–73<br>Remacle et al, Int J Cancer 2000: 89(2): 118–21<br>Luparello et al, Breast Cancer Res Treat 1999; 54(3): 235–44 |

TABLE I-continued

| # | CATEGORY | SPECIFIC EXAMPLES | NOTES (further description; marker forms and identification contexts; assays) |
|---|---|---|---|
| 22 | Chemokine | CC chemokine regulated on activation normal T cell expressed and secreted (RANTES) | Luboshits et al, Cancer Res 1999; 59(18): 4681–7<br>Prest et al, Clin Exp Metastasis, 1999; 17(5): 389–96<br>Luboshits et al, Cancer Res 1999; 59: 4681–4687 |
| 23 | Chemokine | Macrophage inflammatory protein 1 alpha and 2 beta (MIP-1alpha, MIP-2beta) | Tedla et al, Cytokine 1999; 11(7): 531–40<br>Prest et al, Clin Exp Metastasis, 1999; 17(5): 389–96 |
| 24 | Cell adhesion molecule | E-cadherin and N-cadherin | Hazan et al, J Cell Biol 2000; 148(4): 779–90<br>Boterberg et al, Cell Adhes Comm, 2000; 7(4): 299–310 |
| 25 | Basement membrane protein Antibody | LH39 (antibody recognizing the lamina lucida of mature small veins and capillaries | Kakolyris et al, Br J Cancer 2000; 82(4): 844–51 |
| 26 | Basement membrane protein | Laminin | Sidhom and Imam, Int J Clin Lab Res, 1999; 29(1): 26–9<br>Ioachim et al, Anticancer Res 1998; 18(3A): 1665–70 |
| 27 | Cell adhesion molecule | Integrin beta 1 | Berry et al, Eur J Surg Oncol, 2000; 26(1): 25–9 |
| 28 | Cell adhesion molecule | E-selectin | Hebbar et al, Int J Biol Markers, 2000; 15(1): 15–21 |
| 29 | | Catenin (E, alpha, beta, gamma) | Bukholm et al, J Pathol, 2000; 190(1): 15–9 |
| 30 | Receptor | Thrombin receptor | Henrikson et al, Br J Cancer, 1999; 79(34): 401–6 |
| 31 | Protease | Urokinase plasminogen activator (uPA) | Stephens et al, Breast Cancer Res Treat, 1998; 52(1–3): 99–111 |
| 32 | Serpin | Serine protease inhibitors (SERPINS) - alpha-1-antichymotrypsin, alpha-1-antitrypsin, alpha2-macroglobulin, antithrombinIII, C1 inhbitor, alpha2-antiplasmin | Wojtukiewicz et al, Haemostasis 1998; 28(1): 7–13 |
| 33 | Tumor suppressor Tissue specific inhibitor | Mammastatin (polypeptides 47 kD and 65 kD) | Ervin et al, Science 1989; 244(4912): 1585–7 |
| 34 | Protein Nucleic Acid | Cytokeratin | Bac et al, J Korean Med Sci 2000; 15(2): 194–8 |
| 35 | Sialic acid | Lipid bound sialic acid (LSA) | Raval et al, Int J Biol Markers, 1997; 12(2): 61–7<br>Romppanen et al, Anticancer Res, 1997; 17(2B): 1249–53 |
| 36 | DNase | Alkatine DNase (ADA) | Raval et al, Int J Biol Markers, 1997; 12(2): 61–7 |
| 37 | Ribonucleoprotein Enzyme | Telomerase | Mokbel et al, Eur J Surg Oncol 2000; 26(1): 30–3 |
| 38 | Serine protease | Prostate specific antigen (PSA) | Black et al, Breast Cancer Res Treat, 2000; 59(1): 1–14<br>Black et al, Clin Cancer Res, 2000; 6(2): 467–73 |
| 39 | Antibody | Antibody specific for myosin smooth muscle heavy chain (SM1, SM2); Antibody specific for myosin non-muscle (NTM-MyHC) | Chiavegato et al, Virchows Arch 1995; 426(1): 77–86 |
| 40 | Proliferation associated antigen | Endoglin (EDG, CD105) | Matsuno et al, Clin Cancer Res, 1999; 5(2): 371–82 |
| 41 | Nuclear protein | 108 kD, 53 kD, 48 kD nuclear polypeptides | Brys et al, Cytobios 2000; 101(397): 87–94 |
| 42 | Cytoplasmic protein | 36 kD cytoplasmic polypeptide | Brys et al, Cytobios 2000; 101(397): 87–94 |
| 43 | Transforming growth factor alpha family of proteins | Transforming growth factor alpha (TGF-alpha) | Humphreys and Hennighausen, Oncogene 2000; 19(8)<br>Bourhis et al, Int J Cancer 1997; 71(1): 42–8<br>Yoshiji et al, Cancer Res 1996; 56(9); 2013–6 |
| 44 | Transforming growth factor beta family of proteins | Transforming growth factor beta (TGP-beta) | Yoshiji et al, Cancer Res 1996; 56(9); 2013–6<br>Pawlina et al, Mol Cell Endocrinol 1990; 72(1): 55–61 |
| 45 | Protein factor Hormone responsive protein | Colony stimulating factor 1 (CSF-1)<br>M-CSF | Sapi et al, Proc Soc Exp Biol Med 1999; 220(1): 1–8<br>Tang et al, J of Cellular Biochemistry 1992; 50: 350–356<br>Sapi et al, J Soc Gynecol Investig 1998; 5(2): 94–101 |
| 46 | Receptor Hormone responsive protein | Colony stimulating factor receptor (CSF-1R) | Sapi et al, Proc Soc Exp Biol Med 1999; 220(1): 1–8<br>Sapi et al, Cancer Res 1999; 59(21): 5578–85<br>Maher et al, Clin Cancer Res 1998; 4(8): 1851–6<br>Sapi et al, Oncogene 1995; 10(3): 529–42<br>Tang et al, J. of Cellular Biochemistry 1992; 50: 350–356<br>Sapi et al, J Soc Gynecol Investig 1998; 5(2): 94–101<br>Flick et al, Oncogene 1997; 14(21): 2553–61 |
| 47 | Proto-oncogene | c-fms | Sapi et al, Proc Soc Exp Biol Med 1999; 220(1): 1–8<br>Sapi et al, Cancer Res 1999; 59(21): 5578–85<br>Maher et al, Clin Cancer Res 1998; 4(8): 1851–6<br>Sapi et al, Oncogene 1995; 10(3): 529–42 |
| 48 | Phospholipid binding protein Actin binding protein Calcium binding protein | Annexin-1 | Pencil and Toth, Clin Exp Metastasis 1998; 16(2): 113–21<br>Ahn et al, Clin Exp Metastasis 1997; 15(2): 151–6 |
| 49 | Receptor G-protein linked receptor | Vasopressin and Oxytocin receptors | Zingg, Baillieres Clin Endocrinol Metab 1996: 10(1): 75–96 |
| 50 | | Vasopressin: arginine vasopressin (VP), | North et al, Breast Cancer Res Treat 1995; 34(3): 229–5<br>North et al, Breast Cancer Res Treat 1995; 34: 229–235 |

TABLE I-continued

| # | CATEGORY | SPECIFIC EXAMPLES | NOTES (further description; marker forms and identification contexts; assays) |
|---|---|---|---|
| | | provasopression (ProVP), vaopressin-associated human glycopepeptide (VAG) | |
| 51 | | Oxytocin (OT), oxytocin associated human neurophysin (OT-HNP) | North et al, Breast Cancer Res Treat 1995; 34(3): 229–5 |
| 52 | Peptidase | Alanine aminopeptidase (AAP) | Severini et al, Cancer Biochem Biophys 1991; 12(3): 199–204 |
| 53 | Antigen | Tissue polypeptide antigen (TPA or TPS) | Severini et al, Cancer Biochem Biophys 1991; 12(3): 199–204 |
| | | Antigen recognized by M3 antibody | Aydiner et al, Acta Oncol 1994; 33(2): 181–6 |
| 54 | Lactalbumin | Alpha-lactalbumin | Simickova et al, Neoplasma 1991; 38(4): 407–13 |
| 55 | Bcl2 family member Proto-oncogene | Bcl-2 | Schorr et al, J Mammary Gland Biol Neoplasia, 1999; 4(2): 153–64<br>Knowlton et al, J Surg Res, 1998; 76(1): 22–6<br>Veronese et al, Int J Cancer 1998; 79(1): 13–8<br>Olopade et al, Cancer J Sci Am, 1997; 3(4): 230–7<br>Zhang, et al, Clin Cancer Res 1997; 3(12): 2329–35 |
| 56 | Bcl2 family member | Bax | Schorr et al, J Mammary Gland Biol Neoplasia, 1999; 4(2): 153–64<br>Knowlton et al, J Surg Res, 1998; 76(1): 22–6<br>Veronese et al, Int J Cancer, 1998; 79(1): 13–8<br>Olopade et al, Cancer J Sci Am, 1997; 3(4): 230–7 |
| 57 | CCAAT/enhancer binding protein family (C/EBP) | C/EBP | Rosen et al, Biochem Soc Symp 1998; 63: 101–13 |
| 58 | Bone matrix protein | Bone sialoprotein (BSP) | Castronovo and Bellahcene, Int J Oncol 1998; 12(2): 305–8 |
| 59 | Metastasis associated protein Carbohydrate antigen | CA-15-3 | Aydiner et al, Acta Oncol 1994; 33(2): 181–6<br>Guarner et al, Arch Med Res 1997; 28(4): 523–6 |
| 60 | Metastasis associated protein | Beta-2 microglobulin (BMG) | Aydiner et al, Acta Oncol 1994; 33(2): 181–6 |
| 61 | Metastasis associated protein | ferritin | Aydiner et al, Acta Oncol 1994; 33(2): 181–6 |
| 62 | Glycoprotein | P-glycoprotein (MDR1 or MRP gene expression product) | Sikic, Ann Oncol 1999; 10 suppl 6: 149–53<br>Kroger et al, Cancer Treat Rev 1999; 25(5): 279–91 |
| 63 | CCAAT/enhancer binding protein family (C/EBP) | ICBP90 (89, 758 kD) | Hopfner et al, Cancer Res 2000; 60(1): 121–8 |
| 64 | Enzyme | Aromatase (CYP19) | Brueggemeier et al, Cancer Lett 1999; 140(1–2): 27–35 |
| 65 | Enzyme | Cyclo-oxygenase 1,2 (COX-1, COX-2)<br>Prostoglandin endoperoxide synthase | Brueggemeier et al, Cancer Lett 1999; 140(1–2): 27–35<br>Liu and Rose, Cancer Res 1996; 56(22): 5125–7 |
| 66 | Antigen | PGE2 | Brueggemeier et al, Cancer Lett 1999; 140(1–2): 27–35 |
| 67 | Hormone responsive protein | Hormone induced gene-1 (H1-1) | Russo and Russo, J Cell Biochem Suppl 2000; 34: 1–6 |
| 68 | Heat shock protein | BAG-1 (Hsp70/Hsc70) | Krajewski et al, Endocr Relat Cancer 1999; 6(1): 29–40 |
| 69 | Bcl2 family of proteins | Bcl-X(L) | Krajewski et al, Endocr Relat Cancer 1999; 6(1): 29–40 |
| 70 | Caspase | Caspase-3 | Krajewski et al, Endocr Relat Cancer 1999; 6(1): 29–40 |
| 71 | Antigen<br>Tumor rejection antigen | Melanoma associated antigen-1, -3 (MAGE-1, -3)<br>MZ2-E (antigen)<br>MZ2-D (antigen) | Fujie et al, Ann Oncol 1997; 8(4): 369–72<br>Toso et al, Cancer Res 1996; 56(1): 16–20<br>Brassaur et al, Int J Cancer 1992; 52(5): 839–41<br>Gaugler et al, J Exp Med 1994; 179(3): 921–30 |
| 72 | Antigen<br>Tumor injection antigen | SART-1 (800 kD antigen) | Kawamoto et al, Int J Cancer 1999; 80(1): 64–7 |
| 73 | Inhibitor | P16 (INK4, MTS-1)<br>Inhibitor or cyclin D-CDK4 complex | Jaffrain-Rea et al, Clin Endo 1999; 51: 317–325 |
| 74 | Nuclein | Breast cancer specific gene-1 (BCSG-1)<br>gamma-synuclein (SNCG)<br>SNC-gamma | Ji et al, Cancer Res 1997; 57(4): 759–64<br>Lavedan et al, Hum Genet 1998: 103(1): 106–12<br>Jia et al, Cancer Res. 1999; 59(3): 742–7<br>Ji et al, Cancer Res 1997; 57: 759–764 |
| 75 | Peptide | Fibrinogen degradation peptide | WO 98/55872 |
| 76 | Gap junction protein | Connexin 26 | Jamieson et al, J Pathol 1998; 184(1): 37–43 |
| 77 | Gap junction protein | Connexin 43 | Jamieson et al, J Pathol 1998; 184(1): 37–43 |
| 78 | | Fibronectin | Ioachim et al, Anticancer Res 1998; 18(3A): 1665–70 |
| 79 | Inhibitor | Relaxin | Pawlina et al, Mol Cell Endocrinol 1990; 72(1): 55–61 |
| 80 | Growth factor | Fibroblast growth factor - basic (FGFb) | Yoshiji et al, Cancer Res 1996; 56(9); 2013–6 |
| 81 | Antigen<br>Dedifferentiation marker | Carcinoembryonic antigen (CEA) | Kuhajda et al, Cancer 1983; 52: 1257–1264<br>Schmitt and Andrade, J Clin Pathol 1995; 48(1): 53–6<br>Mangili et al, Cancer 1996; 78(11): 2334–9 |
| 82 | Differentiation marker | Human milk fat globulin (HMFG) | DePotter et al, Pathol Res Pract 1988; 183(3): 271–6 |
| 83 | Phosphoprotein<br>Tumor suppressor | p53 | Poller et al, Br J Cancer 1992; 66: 583–588<br>Poller et al, Hum Pathol 1993; 24(5): 463–8 |

TABLE I-continued

| # | CATEGORY | SPECIFIC EXAMPLES | NOTES (further description; marker forms and identification contexts; assays) |
|---|---|---|---|
| | | | Zhang, et al, Clin Cancer Res 1997; 3(12): 2329–35<br>Schmitt et al, J Pathol 1995: 176(3): 233–41<br>Rajan et al, 1997; 42(3): 283–90<br>Rudas et al, Eur J Cancer 1997; 33(1): 39–44<br>Lisboa et al, Virchows Arch 1997; 431(6): 375–81<br>Done et al, Cancer Res 1998; 58(4): 785–9<br>Naidu et al, Anticancer Res 1998; 18(1A): 65–70<br>Jerry et al, Oncogene 2000; 19(8): 1052–8<br>Ioachim et al, Anticancer Res 1998; 18(3A): 1665–70<br>Midulla et al, Anticancer Res 1999; 19(5B): 4033–7 |
| 84 | Receptor | Epidermal growth factor receptor | Poller et al, Br J Cancer 1992; 66: 583–588<br>Poller et al, Hum Pathol 1993; 24(5): 463–8<br>Ioachim et al, Anticancer Res 1998; 18(3A): 1665–70 |
| 85 | Oncogene<br>Oncoprotein | c-erbB-2 | Poller et al, Br J Cancer 1992; 66: 583–588<br>Poller et al, Hum Pathol 1993; 24(5): 463–8<br>Lodata et al, Mod Pathol 1990; 3(4): 449–54<br>Ioachim et al, Anticancer Res 1998; 18(3A): 1665–70<br>Zaretsky et al, FEBS 1990; 265(1–2): 46–50<br>Mangili et al, Cancer 1996; 78(11): 2334–9 |
| 86 | Oncogene<br>Oncoprotein | c-erbB-3 | Naidu et al, Br J. Cancer 1998; 78(10): 1385–90 |
| 87 | Antigen | Her-2/neu | Allred et al, Hum Pathol 1992; 23(9): 974–9<br>Storm et al, Ann Surg Oncol 1995; 2(1): 43–8 |
| 88 | Heat shock protein | Heat shock protein-27 | Storm et al, Ann Surg Oncol 1995; 2(1): 43–8 |
| 89 | Protease | Urokinase plasminogen activator (uPA) | Kennedy et al, British J. of Cancer 1998; 77(10): 1638–1641<br>Bianchi et al, Cancer Res. 1994; 54: 861–866<br>Grondahl et al, Cancer Res. 1993; 53: 2513–2521 |
| 90 | Receptor | Urokinase plasminogen activator receptor (uPAR) | Bianchi et al, Cancer Res. 1994; 54: 861–866 |
| 91 | Proteolytic factor inhibitor | Urokinase-type plasminogen activator (uPA) inhibitor type 1 (PAI-1) | Grondahl et al, Cancer Res. 1993; 53: 2513–2521<br>Harbeck et al, Int J Markers 2000 15(1): 79–83<br>Bianchi et al, Int J. Cancer 1995; 60(5): 597–603<br>Harbeck et al, Breast Cancer Res Treat 1999; 54(2): 147–57 |
| 92 | Whole cell having a marker molecule | Oncofetal ferritin bearing lymphocytes (FBL) | Moroz et al, Cancer 1989; 64(3): 691–7 |
| 93 | Ferritin<br>Antigen | Oncofetal ferritin<br>Placental isoferritin (p43) (PLF) | Moroz et al, Cancer 1989; 64(3): 691–7<br>Auberbach et al, Abstracts and Proceedings from 10th European Cancer Conference Sept. 12, 1999 to Sept. 16. 1999, Vienna Austria; abstract 589<br>Rosen et al, Breast Cancer Res Treat 1992; 24(1): 17–26<br>Reinerova et al, Neoplasma 1996: 43(6): 363–6<br>Rosen et al, Cancer Lett 1991; 59(2): 145–51<br>Stierer et al, Breast Cancer Res Treat 1991; 19(3): 283–8<br>Rosen et al, Cancer Lett 1992; 67(1): 35–45 |
| 94 | Protein | Type IV collagen | Ioachim et al, Anticancer Res 1998; 18(3A): 1665–70 |
| 95 | Proliferation associated antigen | Ki-67 | Ioachim et al, Anticancer Res 1998; 18(3A): 1665–70 |
| 96 | Proliferation associated antigen | PCNA | Ioachim et al, Anticancer Res 1998; 18(3A): 1665–70 |
| 97 | Zinc endoprotease<br>Collagenases<br>Gelatinases<br>Stromelysins<br>Matrilysin<br>Metalloelastase | Matrix metalloproteinase 1, 2, and 3<br>(MMP-1, MMP-2, MMP-3)<br>Collagenases (MMP-1, MMP-8, MMP-13)<br>Gelatinases (MMP-2, MMP-9)<br>Stromelysins (MMP-3, MMP-10)<br>Matrilysin (MMP-7)<br>Metalloelastase (MMP-12)<br>MMP-14 | Brummer et al, Virchows Arch 1999; 435(6): 566–73<br>Jpn J Cancer Res 1999; 90: 516–522<br>Polette et al, Clin Exp Metastasis 1997; 15: 157–163<br>Ueno et al, Cancer Res 1997; 57: 2055–2060<br>Nakopoulou et al, Hum Pathol. 1999; 30(4): 436–442<br>Lee et al, Clin Exp Metastasis 1996 14(6): 512–9<br>Polette et al, Invasion Metastasis 1993; 13(1): 31–7<br>Ioachim et al, Anticancer Res 1998; 18(3A): 1665–70<br>Su et al, Hybridoma 1995; 14(4): 383–390<br>Rha et al, Breast Cancer Res Treat 1997; 43(2): 175–81 |
| 98 | Stromelysin | Stromelysin-3 (ST3)<br>Stromelysin-3 (MMP-11) | Hahnel et al, Int J Cancer 1993; 55(5): 771–4<br>Habnel et al, Int. J Cancer 1994; 58(2): 157–60<br>Kawami et al, Anticancer Res 1993; 13(6A): 2319–23<br>Brummer et al, Virchows Arch 1999; 435(6): 566–73<br>Jpn J Cancer Res 1999; 90: 516–522<br>Polette et al, Clin Exp Metastasis 1997; 15: 157–163<br>Ueno et al, Cancer Res 1997; 57: 2055–2060<br>Nakopoulou et al, Hum Pathol. 1999; 30(4): 436–442<br>Lee et al, Clin Exp Metastasis 1996 14(6): 512–9<br>Polette et al, lnvasion Metastasis 1993; 13(1): 31–7<br>Ioachim et al, Anticancer Res 1998; 18(3A): 1665–70<br>Engel et al, Int J Cancer 1994; 58(6) 830–5<br>Su et al, Hybridoma 1995; 14(4) 383–390 |

TABLE I-continued

| # | CATEGORY | SPECIFIC EXAMPLES | NOTES (further description; marker forms and identification contexts; assays) |
|---|---|---|---|
| 99 | Zinc endoprotease collagenase | MMP-2<br>72 kD<br>type IV collagenase gelatinase | Santavieca et al, Int J Cancer 1995; 64: 336–341<br>Basset et al, Nature 1990: 348: 699–704<br>Talvensaari-Mattila et al, Cancer 1998; 83(6): 1153–62<br>Kawami et al, Anticancer Res 1993; 13(6A): 2319–23<br>Su et al, Hybridoma 1995; 14(4): 383–390 |
| 100 | Kinase | Nm23<br>Nucleoside diphosphate kinase | Hahnel et al, Int. J Cancer 1994; 58(2): 157–60 |
| 101 | Antibody<br>Antigen | Mab 44-3A6 (detecting a 40 kD cell surface protein on adenocarcinomas) | Duda et al, Tumor Biol 1991; 12: 254–260 |
| 102 | Antibody<br>Antigen | Mab A-80 (detecting mucin type glycoprotein; tumor associated cytoplasmic mucin-type glycoprotein)<br>MM 1-80<br>Polymorphic epithelial mucin (PEM) | Shin et al, APMIS 1989; 97(12): 1053–260<br>Eriksson et al, Human Pathol 1992; 23(12): 1366–1372<br>Castagna et al, Path Res Pract. 1992; 188: 1002–1008 |
| 103 | Antibody<br>Antigen | Mab to DF3 (detecting tumor associated antigen 290 kD cell surface protein in breast carcinoma cells; CA15.3 antigen) | Kufe et al, Hybridoma 1984; 3(3): 223–32<br>Ohuchi et al, JNCI (1987); 79(1): 109–115<br>Szpak et al, Acta Cytol. 1984; 28(4): 356–67 |
| 104 | Antibody<br>Antigen | H23 breast tumor associated antigen<br>Gene 17.5 | Zaretsky et al, FEBS 1990; 265(1–2): 46–50<br>Keydar et al, Proc. Natl. Acad Sci USA 1989; 86: 1362–1366<br>Stein et al, Int J Cancer 1991; 47(2): 163–9 |
| 105 | Protein | pS2 | Zaretsky et al, FEBS 1990; 265(1–2): 46–50 |
| 106 | Antibody<br>Antigen | Antibody B72.3<br>Tumor associated glycoprotein-72 (TAG-72)<br>Oncofegal antigen tumor associated glycoprotein-72 | Stein et al, Int J Cancer 1991; 47(2): 163–9<br>Thor et al, Cancer Res 1986; 46: 3118–3124<br>Prey et al, Human Pathol 1991; 22(6): 598–602<br>Contegiacomo et al, Eur J Cancer 1994; 30A(6): 813–820<br>Shousha et al, J Clin Pathol. 1990; 43(12): 1026–8<br>Mangili et al, Cancer 1996: 78(11): 2334–9<br>Szpak et al, Acta Cytol. 1984; 28(4): 356–67<br>Muraro et al, Cancer Res 1988; 48(16): 4588–96<br>Stein et al, Int J Cancer 1991; 47(2): 163–9<br>Lottich et al, Breast Cancer Res Treat 1985; 6(1): 49–56<br>Nuti et al, Int J Cancer 1982; 29(5): 539–45<br>Tavassoli et al, Am J Surg Pathol. 1990; 14(2): 128–33<br>Thor et al, Sem Oncol 1986; 13(4): 393–401 |
| 107 | Antigen | Tn-associated antigen | Konska et al, Int J Oncol 1998; 12(2): 361–7 |
| 108 | | N-acetyl-lactosamine | Konska et al, Int J Oncol 1998; 12(2): 361–7 |
| 109 | Lectin | Lectin | Konska et al, Int J Oncol 1998; 12(2): 361–7 |
| 110 | Receptor | Lectin receptor | Konska et al, Int J Oncol 1998; 12(2): 361–7 |
| 111 | Antibody<br>Antigen | Mab detecting 83D4 antigen | Pancino et al, Hybridoma 1990; 9(4): 389–395<br>Beuzelin-Yuraut et al, J Clin Pathol 1995; 48: 433–437 |
| 112 | Antigen<br>Proteolipid | SP-2 (90 kD antigen) | Iacobelli et al, Cancer Res. 1986: 46: 3005–3010 |
| 113 | Antibody<br>Antigen | Mab 323/A3 (detecting Mr 43 kD glycoprotein) | Edwards et al, Cancer Res 1986; 46(3): 1306–17<br>Courtney et al, Cancer Lett 1991; 57(2): 115–9 |
| 114 | Antigen | Ca-1 | Courtney et al, Br J Cancer Suppl 1990; 10: 92–5 |
| 115 | Antibody<br>Antigen | T-antigen<br>MBE6 antibody | Teramoto et al, Cancer 1982; 50: 241–249 |
| 116 | Receptor | c-met tyrosine kinase receptor | Nakopoulou et al, Histopathology 2000; 36(4): 313–25 |
| 117 | Growth Factor<br>Ligand | Hepatocyte growth factor (HGF) | Nakopoulou et al, Histopathology 2000; 36(4): 313–25<br>Qiao et al, Cell Growth Diff 2000; 11(2): 123–33 |
| 118 | Ligand<br>Nucleic Acid | Angiopoietin-1 | Huang et al, Blood 2000; 95(6): 1993–9 |
| 119 | Nucleic acid<br>Protein | Nm23 | Guo et al, Chung Hua I Hsueh I Chuan Hsueh Tsa Chih 2000; 17(2): 91–93<br>Midulla et al, Anticancer Res 1999; 19(5B): 4033–7 |
| 120 | Protein | Ki67 | Midulla et al, Anticancer Res 1999; 19(5B): 4033–7 |
| 121 | Protein | P21 | Reed et al, Virchows Arch 1999; 435(2): 116–24 |
| 122 | Protein | P27 | Reed et al, Virchows Arch 1999; 435(2): 116–24 |
| 123 | Protein<br>Antibody | TKH1<br>TKH2 | Kjeldsen et al, Cancer Res 1988; 48(8): 2214–20 |
| 124 | Antigen<br>Disaccharide | Sialosyl-Tn | Kjeldsen et al, Cancer Res 1988; 48(8): 2214–20 |
| 125 | Enzyme | Lactate Dehydrogenase (LDH) | Kher et al, Indian J Pathol Microbiol 1997; 40(3): 321–6 |

TABLE I-continued

| # | CATEGORY | SPECIFIC EXAMPLES | NOTES (further description; marker forms and identification contexts; assays) |
|---|---|---|---|
| 126 | Enzyme | Myosin light chain kinase | Nguyen et al, J Cell Biol 1999; 146(1): 149–64 |
| 127 | Tumor suppressor | beta2 microglobulin | Carmon et al, Int J Cancer 2000; 85(3): 391–7 |
| 128 | Protein Peptide | MUC1 | Carmon et al, Int J Cancer 2000; 85(3): 391–7 |

EXAMPLES

1. Retrieval of Ductal Fluid and Analysis of Markers in the Fluid

A patient is prepared for a ductal lavage, using a ductal access tool and a duct on each breast is lavaged and the ductal fluid collected separately from each accessed duct. The fluid in each duct that is accessed is analyzed for nuclear matrix protiens, maspins, maspin, claudin 7, telomerase, basic FGF, fibrinogen degradation peptide, and CSF-1 receptor using standard techniques.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying a patient having breast cancer or breast precancer, said method comprising:
    placing a ductal access tool comprising a single lumen in a breast duct of a patient, wherein the single lumen has an inner diameter large enough to retrieve clusters of greater than 10 cells;
    infusing a fluid into the duct through the single lumen;
    retrieving a ductal fluid sample from the accessed duct through the single lumen, wherein the ductal fluid sample comprises ductal epithelial cells and is free of ductal fluid from any other duct of the breast; and
    examining the ductal fluid sample to determine the presence of a cancer or precancer marker comprising a protein, a polypeptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules.

2. A method for identifying a patient having breast cancer or breast precancer, said method comprising:
    placing a ductal access tool comprising a single lumen in a breast duct of a patient, wherein the single lumen has an inner diameter large enough to retrieve clusters of greater than 10 cells;
    infusing a fluid into the duct through the single lumen;
    retrieving a ductal fluid sample from the accessed duct through the single lumen, wherein the ductal fluid sample comprises ductal epithelial cells and is free of ductal fluid from any other duct of the breast; and
    examining the ductal fluid sample to determine the presence of a marker comprising an RNA, DNA, protein, polypeptide, or peptide form of a marker selected from the group consisting of a receptor, a ligand, a protein factor, an antigen, an antibody, and enzyme, a soluble protein, a cytosolic protein, a cytoplasmic protein, a tumor suppressor, a cell surface antigen, a phospholipid, a lipoprotein, a hormone response protein, a differentiation associated antigen, a proliferation associated antigen, a metastasis associated antigen, an integral membrane protein, a protein that participates in an apoptosis pathway, a protein that participates in a transcriptional activation pathway, a cell adhesion molecule, an extracellular matrix protein, a proteolipid, a cytokine, a basement membrane protein, a mucin-type glycoprotein, a histone, a ribonucleoprotein, a sialic acid, a bone matrix protein, a carbohydrate antigen, a nuclear protein, a nuclear phosphoprotein, a proto-oncogene, an oncogene, an apolipoprotein, a serine protease, a tumor rejection antigen, a surfactant protein, a cell death protein, a zinc endoprotease, and a trefoil gene.

3. A method for identifying a patient having breast cancer or breast precancer, said method comprising:
    placing a ductal access tool comprising a single lumen in a breast duct of a patient, wherein the single lumen has an inner diameter large enough to retrieve clusters of greater than 10 cells;
    infusing a fluid into the duct through the single lumen;
    retrieving a ductal fluid sample from the accessed duct through the single lumen, wherein the ductal fluid sample comprises ductal epithelial cells and is free of ductal fluid from any other duct of the breast; and
    examining the ductal fluid sample to determine the presence of a marker comprising an RNA, DNA, protein, polypeptide, or peptide form of a marker selected from the group consisting of a chemokine, a lectin, an integrin, a selectin, a keratin, an interleukin, a taxin, a ferritin, a lipocalin, a laminin, a cyclin, a relaxin, a nuclein, a caspase, a melanoma-associated antigen, a macrophage inflammatory protein, a gap junction protein, a calcium binding protein, an actin binding protein, a phospholipid binding protein, a heat shock protein, a cell cycle protein, an activator of tyrosine and tryptophan hydroxylase, a member of the tumor necrosis factor family of proteins, a member of the transforming growth factor alpha family of proteins, a member of the transforming growth factor beta family of proteins, a member of the Bcl2 family of proteins, a Bcl2-interacting protein, a Bcl2-associated protein, a member of the vasopressin/oxytocin family of proteins, and a member of the CCAT/enhancer binding protein family of proteins.

4. A method for identifying a patient having breast cancer or breast precancer, said method comprising:
    placing a ductal access tool comprising a single lumen in a breast duct of a patient, wherein the single lumen has an inner diameter large enough to retrieve clusters of greater than 10 cells;

infusing a fluid into the duct through the single lumen;
retrieving a ductal fluid sample from the accessed duct through the single lumen, wherein the ductal fluid sample comprises ductal epithelial cells and is free of ductal fluid from any other duct of the breast; and
examining the ductal fluid sample to determine the presence of a marker comprising an RNA, DNA, protein, polypeptide, or peptide form of a marker selected from the group consisting of a phosphorylase, a phosphatase, a decarboxylase, an isoenzyme, a kinase, a protease, a nuclease, a peptidase, a protease, a DNase, an RNase, an aminopeptidase, a topoisomerase, a phosphodiesterase, an aromatase, a cyclooxygenase, a hydroxylase, a dehydrogenase, a metalloproteinase, a telomerase, a reductase, a synthase, an elastase, a tyrosinase, a transferase, and a cyclase.

5. A method for identifying a patient having breast cancer or breast precancer, said method comprising:
placing a ductal access tool comprising a single lumen in a breast duct of a patient, wherein the single lumen has an inner diameter large enough to retrieve clusters of greater than 10 cells;
infusing a fluid into the duct through the single lumen;
retrieving a ductal fluid sample from the accessed duct through the single lumen, wherein the ductal fluid sample comprises ductal epithelial cells and is free of ductal fluid from any other duct of the breast; and
examining the ductal fluid sample to determine the presence of a marker comprising an RNA, DNA, protein, polypeptide, or peptide form of a marker selected from the group consisting of a steroid hormone receptor, a growth factor receptor, a kinase receptor, a G-protein linked receptor, a TNF family receptor, a tyrosine kinase receptor, a vasopressin receptor, an oxytocin receptor, and a serine protease receptor.

6. A method for identifying a patient having breast cancer or breast precancer, said method comprising:
placing a ductal access tool comprising a single lumen in a breast duct of a patient, wherein the single lumen has an inner diameter large enough to retrieve clusters of greater than 10 cells;
infusing a fluid into the duct through the single lumen;
retrieving a ductal fluid sample from the accessed duct through the single lumen, wherein the ductal fluid sample comprises ductal epithelial cells and is free of ductal fluid from any other duct of the breast; and
examining the ductal fluid sample to determine the presence of a marker comprising an RNA, DNA, protein, polypeptide, or peptide form of a marker selected from the group consisting of a growth factor, a proteolytic factor, a stromal cell factor, an epithelial cell factor, an angiogenesis factor, an epithelial cell factor, an angiogenic factor, and a colony stimulating factor.

7. A method for identifying a patient having breast cancer or breast precancer, said method comprising:
placing a ductal access tool comprising a single lumen in a breast duct of a patient, wherein the single lumen has an inner diameter large enough to retrieve clusters of greater than 10 cells;
infusing a fluid into the duct through the single lumen;
retrieving a ductal fluid sample from the accessed duct through the single lumen, wherein the ductal fluid sample comprises ductal epithelial cells and is free of ductal fluid from any other duct of the breast; and
examining the ductal fluid sample to determine the presence of a marker comprising an RNA, DNA, protein, polypeptide, or peptide form of a marker selected from the group consisting of an inhibitor of a cyclin, an inhibitor of a cyclin complex, a serpin, an inhibitor of proteolytic degradation, a tissue inhibitor of a metalloprotease, and an angiogenesis inhibitor.

8. A method of identifying a patient having breast cancer or breast precancer, said method comprising:
placing a ductal access tool comprising a single lumen in a breast duct of a patient;
infusing a fluid into the duct through the single lumen;
retrieving a ductal fluid sample from the accessed duct through the single lumen, wherein the ductal fluid sample is free of ductal fluid from any other duct of the breast; and
examining the ductal fluid sample to determine the presence of a cancer or precancer marker comprising a protein, a polypeptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules, wherein the presence of the marker in the ductal fluid sample identifies a cytological category selected from the group consisting of normal, abnormal, hyperplasia, atypical ductal carcinoma, ductal carcinoma in situ (DCIS), ductal carcinoma in situ—low grade (DCIS-LG), ductal carcinoma in situ—high grade (DCIS-HG), invasive carcinoma, atypical mild changes, atypical marked changes, and atypical ductal hyperplasia (ADH).

9. The method of claim 1 further comprising analyzing the cells in the ductal fluid sample for abnormal cytology.

10. The method of claim 1 or 8 wherein the method is repeated for more than one duct on a breast.

11. The method of claim 1 or 8 wherein the method is repeated for a plurality of ducts on a breast.

12. A method for identifying a patient having breast cancer or breast precancer, said method comprising:
examining a ductal fluid sample to determine the presence of a cancer or precancer marker comprising a protein, a polypeptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules, wherein the ductal fluid sample is obtained by a method comprising the steps of:
(a) placing a ductal access tool comprising a single lumen in a breast duct of a patient, wherein the single lumen has an inner diameter large enough to retrieve clusters of greater than 10 cells;
(b) infusing a fluid into the duct through the single lumen; and
(c) retrieving the ductal fluid sample from the accessed duct through the single lumen, wherein the fluid sample comprises ductal epithelial cells and is free of ductal fluid from any other duct of the breast.

13. A method of identifying a patient suspected of having breast cancer or breast precancer, said method comprising:
examining a ductal fluid sample to determine the presence of a cancer or precancer marker comprising a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules, wherein the fluid sample is obtained by a method comprising the steps of:

(a) placing a ductal access tool comprising a single lumen in a breast duct of a patient, wherein the single lumen has an inner diameter large enough to retrieve clusters of greater than 10 cells;

(b) infusing a fluid into the duct through the single lumen; and (c) retrieving the ductal fluid sample from the accessed duct through the single lumen, wherein the fluid sample comprises ductal epithelial cells and is free of ductal fluid from any other duct of the breast;

wherein the presence of the marker in the ductal fluid sample identifies a cytological category selected from the group consisting of normal, abnormal, hyperplasia, atypical ductal carcinoma, ductal carcinoma in situ (DCIS), ductal carcinoma in situ—low grade (DCIS-LG), ductal carcinoma in situ—high grade (DCIS-HG), invasive carcinoma, atypical mild changes, atypical marked changes, and atypical ductal hyperplasia (ADH).

14. The method of claim 8 wherein the ductal fluid sample comprises ductal epithelial cells.

15. The method of claim 13 wherein the ductal fluid sample comprises ductal epithelial cells.

16. The method of claim 8 wherein the cytological category is ductal carcinoma in situ—low grade (DCIS-LG).

17. The method of claim 8 wherein the cytological category is ductal carcinoma in situ—high grade (DCIS-HG).

18. The method of claim 8 wherein the cytological category is invasive carcinoma.

19. The method of claim 13 wherein the cytological category is ductal carcinoma in situ—low grade (DCIS-LG).

20. The method of claim 13 wherein the cytological category is ductal carcinoma in situ—high grade (DCIS-HG).

21. The method of claim 13 wherein the cytological category is invasive carcinoma.

22. The method of claim 8 wherein the single lumen has an inner diameter large enough to retrieve clusters of greater than 10 cells.

23. The method of claim 13 wherein the single lumen has an inner diameter large enough to retrieve clusters of greater than 10 cells.

* * * * *

UNITED STATES PATENT AND TRADEMARK OFFICE
CERTIFICATE OF CORRECTION

PATENT NO.    : 6,610,484 B1
DATED         : August 26, 2003
INVENTOR(S)   : David T. Hung It is certified that error appears in the above-identified patent and that said Letters Patent is hereby corrected as shown below:

<u>Column 29,</u>
Line 46, delete "comprising" and replace with -- selected from the group consisting of --.

<u>Column 32,</u>
Lines 16, 42 and 65, delete "comprising" and replace with -- selected from the group consisting of --.

Signed and Sealed this

Thirteenth Day of January, 2004

JON W. DUDAS
*Acting Director of the United States Patent and Trademark Office*